(12) United States Patent
Khazak

(10) Patent No.: US 6,589,773 B1
(45) Date of Patent: Jul. 8, 2003

(54) METHODS AND COMPOSITIONS FOR A MODIFIED YEAST STRAIN WITH INCREASED PERMEABILITY AND USES THEREOF

(75) Inventor: Vladimir Khazak, Brooklyn, NY (US)

(73) Assignee: Morphochem, Inc., Monmouth, NJ (US)

( * ) Notice: Subject to any disclaimer, the term of this patent is extended or adjusted under 35 U.S.C. 154(b) by 0 days.

(21) Appl. No.: 09/502,240

(22) Filed: Feb. 17, 2000

(51) Int. Cl.[7] .............................. C12N 1/20; C12Q 1/68; G01N 33/53; G01N 33/569
(52) U.S. Cl. ............................. 435/252.21; 435/252.2; 435/6; 435/7.31
(58) Field of Search ...................... 435/6, 7.31, 254.21, 435/4, 254.2

(56) References Cited

U.S. PATENT DOCUMENTS 5,871,923 A * 2/1999 Moehle

OTHER PUBLICATIONS

Nourani et al. Multiple–Drug–Resistance phenomenon in the yeast saccharomyces cerevisiae: involvement of two hexose transporters Molecular and Cellular Biology sept. 1997, p. 5453–5460.*

* cited by examiner

*Primary Examiner*—Remy Yucel
*Assistant Examiner*—Konstantina Katcheves
(74) *Attorney, Agent, or Firm*—Edwards & Angell, LLP; Peter F. Corless; Lisa Swiszcz Hazzard

(57) ABSTRACT

The present invention relates to novel yeast cells with increased permeability to compounds, such as small organic compounds. In particular, the invention provides genetically modified yeast cells carrying functional, preferably conditionally regulated, copies of HXT9 and HXT11 genes integrated in the chromosome at the PDR1 and PDR3 loci, thereby disrupting the PDR1 and PDR3 gene activity. The invention further relates to methods and compositions for the use of these hyperpermeable yeast cells for screening for compounds that modulate macromolecular interactions. The invention is exemplified by the use of the hyperpermeable yeast cells in such a screening system. In addition, the invention further provides methods of producing the yeast cells of the invention, as well as polynucleotides, vectors, and kits for use of the hyperpermeable yeast cells and the screening methods of the invention.

28 Claims, 16 Drawing Sheets

SEQUENCE LISTING

<160> NUMBER OF SEQ ID NOS: 16

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 1
ctcaagctta tgtcaggtgt taataataca tcc                33

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 2
ccgaaaactt ctagatcagc tggaaaag                28

<210> SEQ ID NO 3
<211> LENGTH: 28

```
<212> TYPE: DNA
<213> ORGANISM: Artificial Sequence
<220> FEATURE:
<223> OTHER INFORMATION: Description of Artificial Sequence: Primer

<400> SEQUENCE: 3
cttacccaag cttatgtccg gtgttaat                                              28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 4
acctctagat tagctggaaa agaacctc                                              28

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5 ttaattttt cttattgcgt gaccg                                                  25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
tggttatgct ctgcttccct atttc                                                 25

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 7
aaaggatcct tttatgtgga agacccgca                                             29

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 8
tttggatcca ttaacatcga tgaacccgtg t                                          31

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 9
```
cagaaaagaa tccaagaaac tggaag                                              26

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 10
gagaactttt atctatacaa acgtatacg                                           29

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 11
tttggatcct gacaatcgtc actcg                                               25

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 12
ttaggatcct cacaagggc tgcggta                                              27

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 13
ggaagaatta tttctggcct agg                                                 23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
aatagacacg tacggcgtcc                                                     20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
ggaagaggtt atcgccctgc                                                     20

<210> SEQ ID NO 16
<211> LENGTH: 18
<212> TYPE: DNA
<213> ORGANISM: Artificial Sequence

```
<220> FEATURE:
<223> OTHER INFORMATION: Description of Artificial Sequence: Primer

<400> SEQUENCE: 16
ccctgcactg taccccc                                                    18
```

METHODS AND COMPOSITIONS FOR A MODIFIED YEAST STRAIN WITH INCREASED PERMEABILITY AND USES THEREOF

1. INTRODUCTION

The present invention relates to novel yeast cells with increased permeability to compounds, such as small organic compounds. In particular, the invention provides genetically modified yeast cells carrying functional, preferably conditionally regulated, copies of HXT9 and HXT11 genes integrated in the chromosome at the PDR1 and PDR3 loci, thereby disrupting the PDR1 and PDR3 gene activity. The invention further relates to methods and compositions for the use of these hyperpermeable yeast cells for screening for compounds that modulate macromolecular interactions. The invention is exemplified by the use of the hyperpermeable yeast cells in such a screening system. In addition, the invention further provides methods of producing the yeast cells of the invention, as well as polynucleotides, vectors, and kits for use of the hyperpermeable yeast cells and the screening methods of the invention.

2. BACKGROUND OF THE INVENTION

With recent advances in genome-wide sequencing, studies of protein function and macromolecular interactions have become increasingly important for understanding biological function and for identifying novel therapeutic targets. Screening assays in microbial organisms have been developed to allow rapid identification of genes and gene products involved in various biological activities, including regulation of gene expression, signal transduction, catalysis, and macromolecular interactions important for cellular growth and regulation. For example, a yeast-based screening assay, the so-called yeast two-hybrid screen, has been developed to identify and analyze protein-protein interactions (Fields and Song, 1989, Nature 340:245–246; U.S. Pat. No. 5,468,614). This method allows screening and identification of proteins that specifically interact with a target protein of interest, and has recently been expanded to allow detection of interactions between proteins and RNA (SenGupta et al., 1996, Proc. Natl. Acad. Sci. U.S.A. 93: 8496–8501; Wang et al., 1996, Genes Dev. 10: 3028–3040), proteins and nonprotein ligands (Meyerson et al., 1992, EMBO J. 11: 2909–2917), proteins and peptides (Colas et al., 1996, Nature 380: 548–550; Yang et al., 1995, Nucleic Acids Res. 23: 1152–1156), proteins and multiple partners (Osborne et al, 1996, J. Biol. Chem. 271: 29271–29278; Tirode et al., 1997, J. Biol. Chem. 272: 22995–22999), and whole-genome applications (Finley et al., 1994, Proc. Natl. Acad. Sci. USA 91: 12980–12984; Bartel et al., 1996, Nat. Genet 12: 72–77; Fromont-Racine et al., 1997, Nat. Gen. 16: 277–282).

However, less progress has been made at attempts to adapt such yeast screening techniques for use in high-throughput screens for identifying therapeutic drug candidates. A major reason for lack of success in this area is the impermeability of yeast to most organic molecules. To design successful screening techniques in yeast, therefore, the yeast cell membrane must be made accessible to such molecules. Compounds must be able, first, to cross the yeast membrane, and second, once inside the cell, to escape elimination by the yeast detoxification, through metabolic or exocytotic pathways.

Physical and chemical genetic techniques have been used to enhance the permeability of yeast membranes. Permeabilizing agents, such as Polymyxin B sulfate and Polymyxin B nonapeptide, have been used to physically disrupt the integrity of yeast membranes (Boguslawski, 1985, Mol. Gen. Genet. 199:401–405). In addition, yeast genetics and molecular biology techniques have been used to identify genes involved in membrane permeability, and yeast strains have been isolated bearing mutations in such transport pathway genes (e.g., see Brendel, 1976, Mol. Gen. Genet. 147:209–15). A number of yeast genes have been found to be involved in the biosynthesis, maintenance, and degradation of the cell wall and plasma membrane (Lees et al., 1992, ACS SYMP. Ser. 497:246–259; see also, e.g., U.S. Pat. No. 5,821,038), as well as pathways controlling detoxification of organic molecules.

Membrane transport systems are classified into three classes: channels, facilitators, and pumps (Andre, 1995, Yeast 11:1575–1611). Channels are complexes of membrane proteins that mediate passive transport of ions by forming an aqueous diffusion pore. Facilitators mediate the diffusion of solutes across membranes. Many of the facilitators belong to a family, called the Major Facilitator Super-family (MFS), which possess a common structural topology: two 6-transmembrane-spanning helical segments connected by a cytoplasmic loop (Marger and Saier, 1993, Trends Biochem. Sci. 18:13–20). In S. cerevisiae, a network of regulators associated with the phenotype known as pleiotropic drug resistance (PDR), which closely resembles the mammalian MFS, is known to affect cellular transport and drug resistance. Pdr1p and Pdr3p, members of the C6 zinc cluster family of transcriptional regulatory proteins, modulate expression of ABC transporter genes at the transcriptional level (Saunders and Rank, 1982, Can. J. Genet. Cytol. 24:493–502; Katzmann et al., 1994, Mol. Cell. Biol. 14: 4653–4661). Disruption of PDR1 and PDR3, the genes encoding pdr1p and Pdr3p, respectively, results in decreased expression of the ABC transporter PDR5, and thereby increases drug sensitivity of these cells (Nourani et al., 1997, Mol. Cell. Biol. 17:5453–5460). However, expression of two MFS genes from the hexose transporter (HXT) family (Kruckeberg, 1996, Arch. Microbiol. 166:283–292), HXT9 and HXT11, is also regulated by pdr1p and Pdr3p (Nourani et al., 1997, Mol. Cell. Biol. 17:5453–5460). Overexpression of HXT11 in wild-type yeast causes increased drug sensitivity, and, conversely, the loss of either or both of HXT9 and HXT11 expression results in increased drug resistance (Nourani et al., 1997, Mol. Cell. Biol. 17:5453–5460).

Pumps are split amongst two sub-classes, the ATP-Binding Cassette (ABC) transporters and other P-type ATPases, both of which transport solutes against chemical gradients by hydrolysis of ATP. Genes involved in many of these pathways can be modified genetically to alter cellular permeability. Furthermore, it has been reported that the modification of at least two particular genes which control cellular permeability at different levels (i.e., cell wall synthesis or maintenance; plasma membrane synthesis or maintenance; and detoxification or export of endogenous compounds) results in a synergistically increased effect on permeability (see, e.g., U.S. Pat. No. 5,821,038). However, despite such efforts, there is an urgent need to develop new methods for permeabilizing yeast cells for designing high-throughput screening techniques for therapeutic compounds in yeast.

A second major difficulty encountered in attempts at adapting yeast screening technologies into high-throughput screening for candidate therapeutic compounds is the high background of "false positives" that typically result from such screens. High backgrounds of non-specific interactions, or "false positives", are a particular problem with yeast two-hybrid screening methods. Currently available methods for screening for molecules that disrupt macromolecular interactions are labor-intensive, and the high backgrounds of non-specific interactions necessitate multiple screening steps. Typically, an initial screen is necessary to identify candidate inhibitors of a target interaction of interest. This screen is then followed by further screening steps to eliminate the false positives. Furthermore, since compounds potentially useful as therapeutics are likely to have relatively weak interactions with their target, identification of drug candidates is even less likely to be successful using this multistep screening procedure.

Therefore, despite great interest and effort in this field, no efficient, sensitive, versatile high-throughput screening system has yet been described for identifying compounds that modulate macromolecular interactions in yeast.

3. SUMMARY OF THE INVENTION

The present invention relates to novel hyperpermeable yeast cells useful for screening for small molecules that modulate macromolecular interactions. The invention is based, in part, on the discovery that the concomitant insertion of functional, preferably conditionally regulated, copies of two yeast genes, involved in hexose transport, into particular genetic loci encoding transcriptional regulators of pleiotropic drug resistance, increases cellular permeability, such as permeability of small molecules. The resultant double insertion/disruption renders the novel cells more permeable to compounds, such as small molecules, than either genetic alteration alone.

The invention provides hyperpermeable yeast cells with increased permeability to compounds such as small molecules. Such hyperpermeable yeast cells are constructed by inserting one or more copies of genes that can increase cellular permeability, and concomitantly disrupting one or more endogenous genes that can decrease cellular permeability. In particular, a hyperpermeable yeast cell comprises a functional HXT9 hexose transporter gene, a functional HXT11 hexose transporter gene; a disrupted PDR1 pleiotropic resistance gene, and a disrupted PDR3 pleiotropic resistance gene, wherein the functional HXT9 gene or the functional HXT11 gene is chromosomally integrated into the disrupted PDR1 gene or the disrupted PDR3 gene.

In one embodiment, the hyperpermeable yeast cell comprises a HXT9 gene chromosomally integrated into the disrupted PDR1 gene, and further comprises an inactivated PDR3 gene and an independently regulated functional HXT11 gene.

In another embodiment, the hyperpermeable yeast cell comprises a HXT9 gene chromosomally integrated into the disrupted PDR3 gene and further comprises an inactivated PDR1 gene and an independently regulated functional HXT11 gene.

In another embodiment, the hyperpermeable yeast cell comprises a HXT11 gene chromosomally integrated into the disrupted PDR1 gene and further comprises an inactivated PDR3 gene and an independently regulated functional HXT9 gene.

In another embodiment, the hyperpermeable yeast cell comprises a HXT11 gene chromosomally integrated into the disrupted PDR3 gene and further comprises an inactivated PDR1 gene and an independently regulated functional HXT9 gene.

In a specific embodiment, the hyperpermeable yeast cell comprises a HXT9 gene chromosomally integrated into the disrupted PDR1 gene, and further comprises a independently regulated functional HXT11 gene chromosomally integrated into a disrupted PDR1 gene.

In another specific embodiment, the hyperpermeable yeast cell comprises a independently regulated functional HXT9 gene chromosomally integrated into the disrupted PDR3 gene, and further comprises a independently regulated functional HXT11 gene chromosomally integrated into a disrupted PDR1 gene.

In yet another specific embodiment, a hyperpermeable yeast cell comprises independently regulated functional HXT9 and HXT11 genes chromosomally integrated into the PDR1 locus, and further comprises a disrupted PDR3 gene.

In yet another specific embodiment, a hyperpermeable yeast cell comprises independently regulated functional HXT9 and HXT11 genes chromosomally integrated into the PDR3 locus, and further comprises a disrupted PDR1 gene.

The invention further provides methods for construction of such yeast cells, comprising inserting HXT9 and HXT11, operably associated with a conditionally regulated promoter into the yeast chromosome at the position of PDR1 and PDR3, respectively, such that the genes PDR1 and PDR3 are disrupted.

The invention further encompasses kits and methods the use of hyperpermeable yeast cells and for screening assays for organic molecules.

The invention is illustrated by a working example provided herein of the engineering of a cell of the yeast S. cerevisiae constructed by inserting HXT9 and HXT11 into the PDR1 and PDR3 loci, respectively. The yeast cells of the invention can be used in any of a number of screening methods, including, for example, enzymatic assays, transcriptional assays, or translational activities, and assays for protein-protein interactions, protein-RNA interactions, protein-nonprotein interactions, protein-peptide interactions, and screening assays for modulators thereof. The invention is further illustrated by an example in which the novel hyperpermeable yeast cells of the invention are used as a host background for a successful yeast two-hybrid dual-bait screening system.

The methods described herein utilize methods and compositions for identifying compounds that modulate macromolecular interactions (e.g., either homotypic or heterotypic protein-protein interactions). For simplicity of description, one protein involved in the protein-protein interaction of interest is referred to herein as a "target protein" and a second protein involved in the protein-protein interaction of interest is referred to herein as a "partner protein." It will be understood that the term "target protein" can be considered interchangeable with the term "partner protein" for the purposes of the methods and compositions described herein. It is also to be understood that the terms can refer to the full-length proteins involved in the protein-protein interactions, or to portions thereof that still exhibit the protein-protein interactions of interest.

As used herein, a "functional" copy of a hexose transporter gene, e.g., HXT9 or HXT11, refers to one which can express in either a constitutive, conditionally regulated (e.g., inducible) manner, a polypeptide exhibiting hexose transporter activity, e.g., HXT9 or HXT11 activity.

As used herein, "hyperpermeable" yeast cells or a "hyperpermeable" yeast strain, are yeast cells and strains which have an increased sensitivity to one or more test compounds, relative to the sensitivity of the yeast cells and strains without the above-described insertion-disruption of genes that alter cellular permeability. Sensitivity to such compounds and small molecules is determined by measuring the MIC (minimal inhibitory concentration) of such compounds to visible growth of yeast cells, disregarding a haze of barely visible growth of such yeast cells.

4. DESCRIPTION OF THE FIGURES

FIGS. 1A–E depict the first step of the integrative transformation strategy used to construct the modified yeast strains SKY54 and SKY197: the HXT9 gene is targeted to the yeast PDR1 locus. (A) Plasmid vector containing upstream (5') and downstream (3') flanking regions of the PDR1 gene separated by a unique restriction site (BamHI). (B) The integrative cassette containing hisG-URA3-cadA is inserted at the unique BamHI site between the PDR1 gene fragments. (C) The structure of recombination intermediate containing a PDR1 gene disrupted by the hisG-URA3-cadA cassette. (D) Recombination between hisG and cadA sequences of the hisG-URA3-cadA cassette on the chromosome and the linear hisG-HXT9-cadA cassette results in insertion of HXT9 into the chromosomal location of the PDR1 gene. (E) The genomic structure of the PDR1 locus of the modified yeast strains SKY54 and SKY197.

FIGS. 2A–E depict the second step of the integrative transformation strategy used to construct the modified yeast strains SKY54 and SKY197: the HXT11 gene is targeted to the yeast PDR3 locus. (A) Plasmid vector containing upstream (5') and downstream (3') flanking regions of the PDR3 gene separated by a unique restriction site (BamHI). (B) The integrative cassette containing hisG-URA3-Int is inserted at the unique BamHI site between the PDR3 gene fragments. (C) The structure of recombination intermediate containing a PDR3 gene disrupted by the hisG-URA3-Int cassette. (D) Homologous recombination between hisG and Int sequences of the hisG-URA3-Int cassette on the chromosome and the linear hisG-HXT11-cadA cassette results in insertion of the HXT11 gene at the endogenous yeast PDR3 locus. (E) The genomic structure of the PDR3 locus of the modified yeast strains SKY54 and SKY197.

FIG. 3 map of the pGem5-3-PDR1 plasmid. The upstream fragment (PDR1-5') and the downstream fragment (PDR1-3') are indicated, on either side of the unique BamHI site.

FIG. 4 map of the pHisCadA plasmid. The *E. coli* cadBA gene operon (cadA) is inserted downstream from the Salmonella hisG and yeast URA3 genes, as indicated.

FIG. 5 map of the pPDR1-HisCadA plasmid. The hisG-URA3-cadA gene fragment is flanked by upstream (PDR1-5') and downstream (PDR1-3') sequences of PDR1, as indicated.

FIG. 6 map of the pGEM5-3-PDR3 plasmid. The upstream fragment (PDR3-5') and the downstream fragment (PDR3-3') are indicated, on either side of the unique BamHI site.

FIG. 7 map of the pHis-Int plasmid. The human immunodeficiency virus (HIV) integrase gene (INT) is inserted downstream from the Salmonella hisG and yeast URA3 genes, as indicated.

FIG. 8 map of the pPDR3-HisInt plasmid. The hisG-URA3-Int gene fragment is flanked by upstream (PDR3-5') and downstream (PDR3-3') sequences of PDR3, as indicated.

FIG. 9 map of the pYES-HXT9 plasmid. The HXT9 gene fragment (HXT9) is inserted downstream from the inducible galactose-1 promoter (P GAL1) and upstream of the CYC transcription terminator sequence (TT).

FIG. 10 map of the pHisCadA-HXT9 plasmid. The P GAL1-HXT9-TT is inserted upstream from *E. coli* cadBA gene operon (cadA).

FIG. 11 map of the pYes-HXT11 plasmid. The HXT11 gene fragment (HXT11) is inserted downstream from the inducible galactose-1 promoter (P GAL1) and upstream of the CYC transcription terminator sequence (TT).

FIG. 12 map of the pHisInt-HXT11 plasmid. The P GAL1-HXT11-TT is inserted upstream from human immunodeficiency virus (HIV) integrase gene sequences (INT).

Figure 15:

FIG. 15 demonstrates the sensitivity of the modified yeast cells, relative to the unmodified parental strains, to various compounds. Decreasing concentrations of cycloheximide, 4-nitroquinolin-oxide, sulfmethuron methyl, and Zeocin were plated on parental yeast strains SKY48 and SKY191 and the modified yeast strains SKY54 and SKY197. From top to bottom of each plate, and from left to right of each row: 5 µg, 2.5 µg, 1 µg, 0.5 µg, 0.2 µg, and 50 ng of CYH; 2.5 µg, 1.25 µg, 0.5 µg, 0.25 µg, 0.1 µg, and 25 ng of NQO; 100 µg, 50 µg, 20 µg, 10 µg, 4 µg, and 1 µg of SMM; and 100 µg, 50 µg, 20 µg, 10 µg, 4 µg, and 1 µg of Zeo.

Figure 16A:
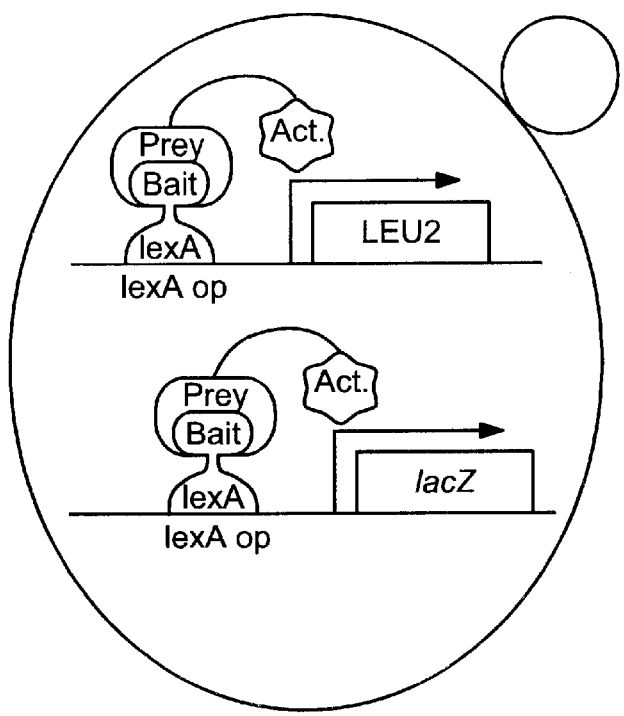
Figure 16B:
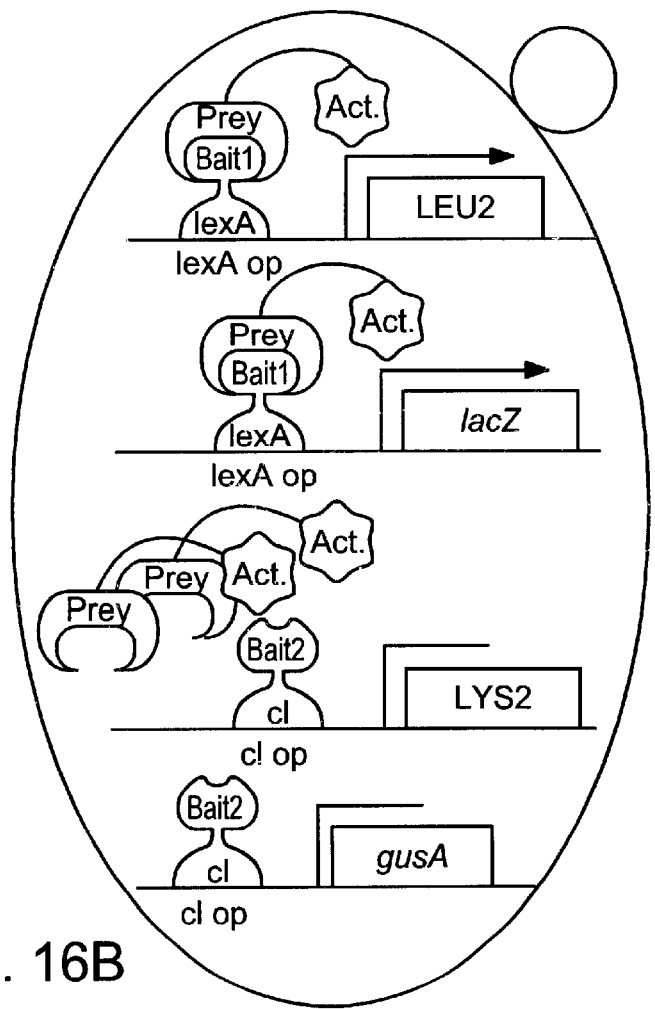

FIGS. 16A–B depicts the internally controlled dual-bait two hybrid system. A) A LexA-fused "Bait" (the target protein) interacts with an Activation Domain (Act.)-fused "Prey" (the partner protein) to activate transcription of lexA operator (lexA op)-responsive LEU2 and lacZ reporter genes. A test compound that interferes with the Bait-Prey interaction will decrease expression from both reporters, resulting in a LEU-LacZ-phenotype. B) An activation domain (Act.) fusion protein ("Prey") interacts with a LexA fusion protein ("Bait 1") to direct transcription of LexA operator (lexA op)-responsive LEU2 and LacZ reporter genes but does not interact with cI fusion protein ("Bait 2") and, thus, does not activate transcription of cI operator (cI op)-responsive LYS2 and gusA reporter genes.

5. DETAILED DESCRIPTION OF THE INVENTION

Described in this Section are methods and compositions for the construction of novel hyperpermeable yeast cells, and yeast screening systems useful for high-throughput screening for compounds that modulate macromolecular interactions.

In particular, described herein in Section 5.1, are compositions and methods for constructing genetically engineered hyperpermeable yeast cells containing functional, preferably inducible, copies of the genes HXT9 and HXT11, and the concomitant disruption of genes PDR1 and PDR3, two genes involved decreasing cellular permeability. The resultant double insertion/disruption renders the novel yeast cells more permeable than either genetic alteration alone.

Section 5.2 describes methods for use of the novel yeast cells in screening for potentially therapeutic compounds. In particular, a novel yeast dual-bait two-hybrid selection system is described, which provides, in a single screen, a selection for compounds that modulate macromolecular interactions, and a selection against non-specific interactions.

Exemplary small molecules and compounds are described in detail in Section 5.3, below. Section 5.4 describes kits that can be used for identification of therapeutic compounds.

5.1 Hyperpermeabile Yeast

As described herein, the chromosomal expression of the hexose transporters HXT9 and HXT11 with the concomitant loss of the pleiotropic drug resistance (PDR) transcription factors PDR1 and PDR3 results in modified yeast cells that are hyperpermeable to compounds such as small molecules. Thus, the simultaneous inactivation of PDR1 and PDR3 and presence of functional copies of HXT9 and HXT11, renders the cells hyperpermeable, i.e., more permeable than either modification alone. In such cells, one or more of the functional hexose transporter genes is inserted within one or more of the PDR genes, thereby disrupting the PDR gene or genes. Preferably, the functional hexose transporter genes are conditionally regulated, e.g., inducible. Moreover, the chromosomal location of the hexose transporters in these cells (as opposed to residing on high-copy episomes under constitutive promoters) facilitates the introduction of recombinant genes that can be used in screening for small molecule therapeutic candidates into such cells.

The hyperpermeable yeast cells described herein are the products of inactivation of pdr1p and Pdr3p, transcriptional regulators of pleiotropic drug resistance, and the concomitant activation of hexose transporter genes, two yeast genes known to increase small molecule permeability. Disruption of PDR1 and PDR3, the genes encoding pdr1p and Pdr3p, respectively, results in decreased expression of the ABC transporter PDR5, and thereby increases drug sensitivity of these cells (Nourani et al., supra). However, expression of two MFS genes from the hexose transporter (HXT) family, HXT9 and HXT11, is also regulated by pdr1p and Pdr3p. Overexpression of HXT11 in wild-type yeast causes increased drug sensitivity, and, conversely, the loss of either or both of HXT9 and HXT11 expression results in increased drug resistance (Nourani et al., supra). Thus, in yeast cells with a simple deletion of either or both of PDR1 or PDR3, the increase in permeability resulting from decrease in expression of ABC transporter genes is offset by a decrease in permeability resulting from the loss of HXT9 and HXT11 expression. However, as described herein, the simultaneous inactivation of PDR1 and PDR3 and activation of HXT9 and HXT11 results in hyperpermeable yeast cells.

The present invention encompasses yeast cells and strains in which either or both PDR1 or PDR3 are disrupted, and independently regulated, functional copies of either or both HXT9 or HXT11, are activated in the yeast genome. As used herein, a "functional" copy of a hexose transporter gene, e.g., HXT9 or HXT11, refers to one which can express in either a constitutive, conditionally regulated (e.g., inducible) manner, a polypeptide exhibiting hexose transporter activity, e.g., HXT9 or HXT11 activity. As used herein, an "independently regulated" gene refers to a gene that is operably linked to a regulatory control element which is not under the control of the PDR that controls its expression from its native promoter. For example, an "independently regulated" HXT9 gene is regulated in a PDR1-independent manner, and an "independently regulated" HXT11 gene is regulated in a PDR3-independent manner.

In one embodiment, for example, either or both PDR1 or PDR3 are disrupted, and replaced by independently regulated and functional copies of either or both HXT9 or HXT11, in either genetic locus. Techniques for the genetic manipulation of yeast, i.e., recombinant expression, including regulatable expression, are well known in the art, and are described generally in standard texts such as Tuite and Oliver, 1991, Biotechnology Handbooks: Saccharomyces, vol. 4, Plenum Press, New York; Kaiser, 1994, "Methods in Yeast Genetics," Cold Spring Harbor Laboratory Press, New York; and Spenser, 1989, "Yeast Genetics," Springer-Verlag, New York, each of which is incorporated herein by reference in its entirety. Standard techniques can also be utilized for manipulation and maintaining yeast cells.

For example, inactivation of PDR gene expression can be achieved by various methods such as, but not limited to, mutagenesis and selection, site-directed mutagenesis, or homologous recombination of the PDR gene coding region or its regulatory region. Techniques for gene disruption and gene replacement using homologous recombination are well known (Scherer and Davis, 1979, Proc. Natl. Acad. Sci. U.S.A. 76:4951–4955; Rothstein, 1983, Meth. Enzym. 101: 202–211; Russell and Nurse, 1986, Cell 45:145–153). Similarly, activation of hexose transporter gene expression can be achieved by standard recombinant techniques. In one embodiment, for example, a functional copy of a HXT gene under the control of a heterologous or native promoter element can be inserted in the yeast chromosome or other replicon. In an alternative embodiment, an independently regulated HXT gene is constructed by activation of a HXT gene in its native location by inserting a control element upstream of the native HXT gene coding region.

In one embodiment, using the technique of gene replacement, functional copies of the HXT9 and HXT11 genes, preferably inducible, can be inserted by homologous recombination into the yeast genome, at the chromosomal sites of PDR1 and PDR3, respectively, which are thereby simultaneously disrupted. In another embodiment, functional copies of both the HXT9 and HXT11 genes can be inserted into the same locus, either PDR1 or PDR3, PDR1 and PDR3 genes can be disrupted by any method known in the art for disruption gene function.

Figure 1A:
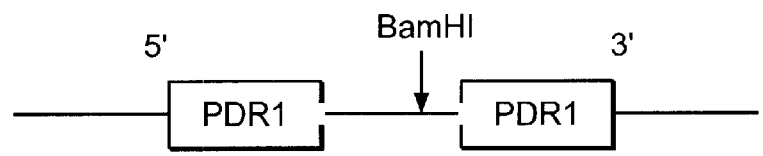
Figure 1B:
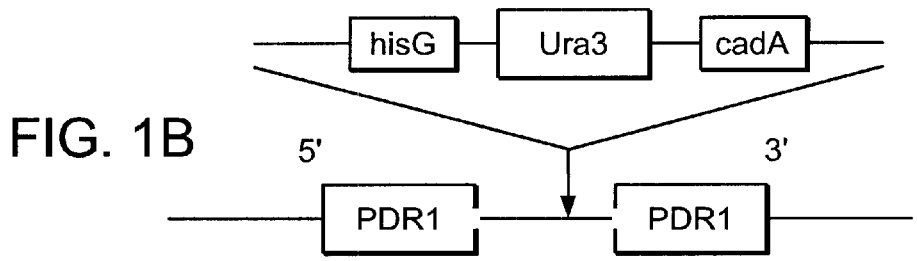
Figure 1C:
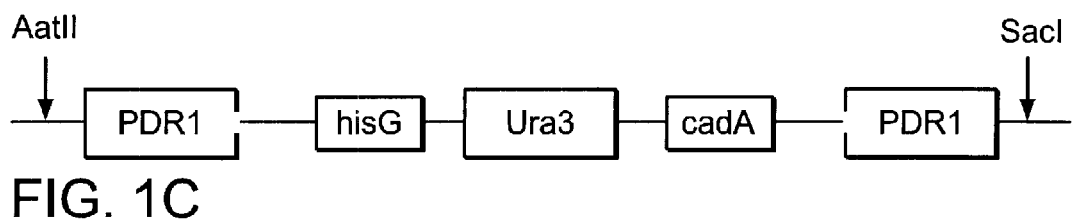

In a specific embodiment, for example, the HXT9 gene is integrated into the chromosome locus of the PDR1 gene and the HXT11 gene is targeted to the chromosome locus of the and PDR3 gene in a pair of two-step integrative transformation steps. This strategy for targeted replacement of the PDR1 gene with HXT9 is outlined in FIG. 1. An integrative cassette, as shown in FIGS. 1A–B, containing a selectable marker gene (URA3) flanked on either side by unique sequences (in this case sequences from the Salmonella hisG and the E. coli cadA genes), is inserted at a unique restriction site (BamHI) between upstream and downstream sequences corresponding to the PDR1 gene. Such an integrative cassette can be constructed as follows:. first, specific primers to the PDR1 gene are designed and synthesized, and used to PCR amplify the upstream and downstream flanking regions of the PDR1 gene. The PCR fragments are then cloned into a cloning vector so that a unique restriction site is located between the two fragments (FIG. 1A). Next, an integrative cassette is constructed by inserting a selectable marker gene flanked on either side by Salmonella hisG and E. coli cadA gene sequences, respectively, is cloned into the cloning vector at the unique restriction site between the PDR1 gene flanking regions (FIG. 1B). Finally, the entire PDR1 integrated cassette fragment is excised from the plasmid (FIG. 1C), purified, and transformed into a parental yeast strain capable of homologous recombination. When linearized fragments containing homology to a region of chromosomal DNA are transformed into such a yeast cell, they undergo homologous mitotic recombination through the double strand break repair pathway (see Orr-Weaver and Szostak, 1985, Microbiol. Rev. 49:33–58). Selection for expression of the selectable marker present within the integrative cassette results in isolation of colonies in which the homologous recombination event has taken place.

Figure 1D:
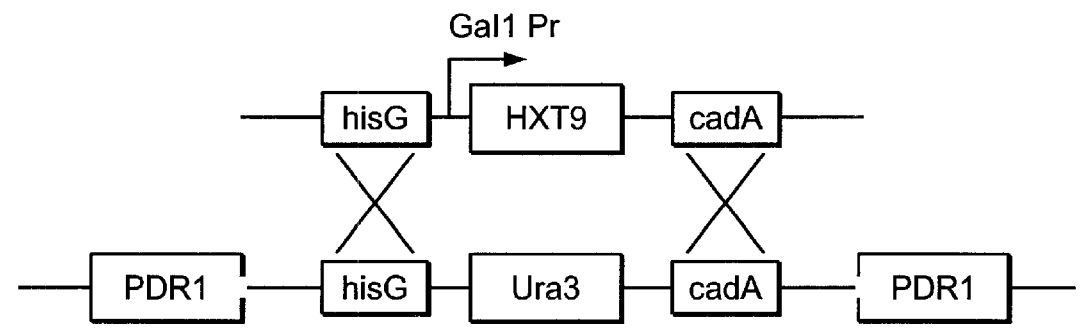
Figure 1E:
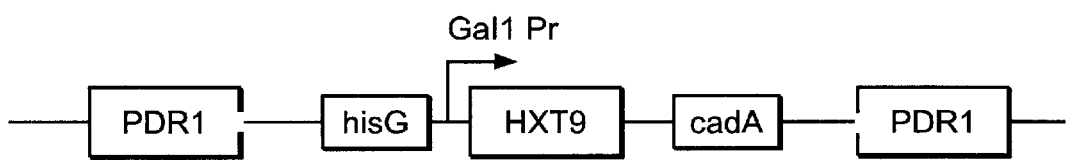
Figure 2A:
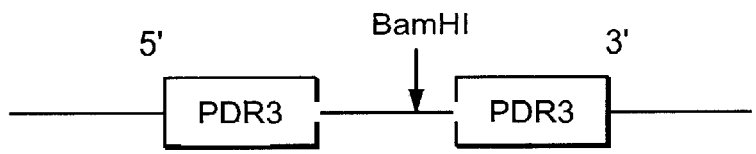
Figure 2B:
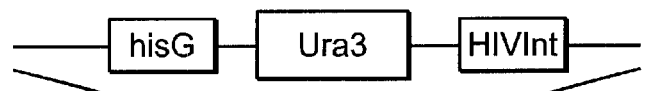
Figure 2C:
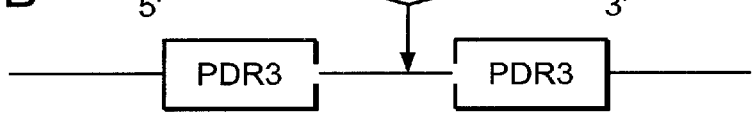
Figure 2D:
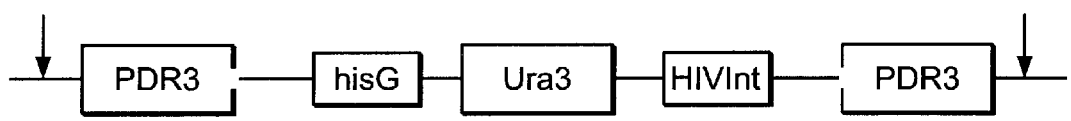
Figure 2D:
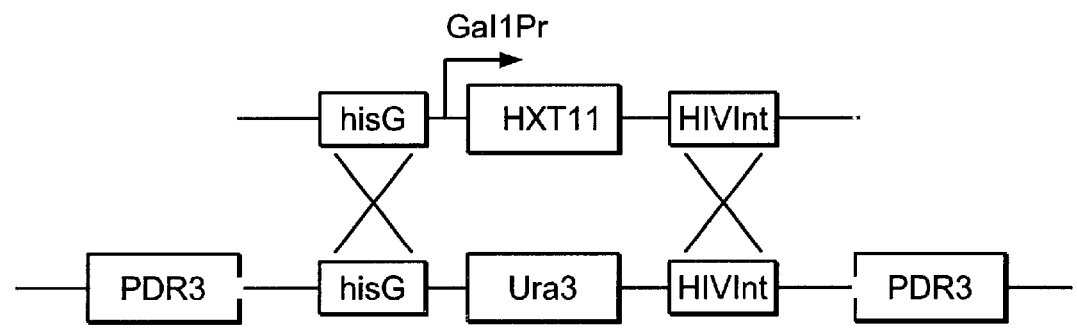
Figure 2E:
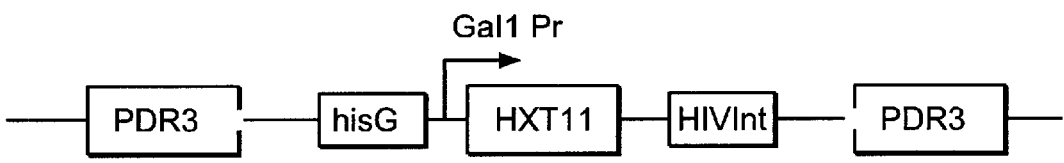

In the second step, an integrative cassette is constructed for insertion of the HXT9 gene into the interrupted PDR1 gene, by homologous recombination of the flanking regions of homology, the Salmonella hisG and E. coli cadA gene sequences. This can be accomplished by construction of a second integrative cassette, containing the coding sequence of HXT9, preferably immediately downstream of, and under the control of, an inducible promoter, and immediately upstream of a transcription terminator (TT) sequence. The cassette containing the recombinant HXT9 gene sequences is excised, purified, and ligated into a vector between the Salmonella hisG and E. coli cadA gene sequences. The entire HXT9 integrative cassette is excised from the vector, purified and transformed into the yeast cell constructed in the first step, above (FIG. 1D). Again, homologous recombination at the flanking markers will occur, this time replacing the URA3 marker with the HXT9 gene (FIG. 1E). Yeast cells that have undergone homologous recombination at the PDR1 locus can be isolated by selection against URA3.

This entire procedure can be performed using constructs similar to those described above, which target HXT11 to the PDR3 locus. The strategy for this integrative transformation is outlined in FIGS. 2A–E. Preferably, the two integrative transformations are done in a single strain, resulting in the double mutant containing inducible copies of HXT9 and HXT11, and disrupted PDR1 and PDR3 genes.

As noted above, a "functional" copy of a hexose transporter gene, e.g., HXT9 or HXT11, refers to one which can express in either a constituitive, conditionally regulated (e.g., inducible) manner, a polypeptide exhibiting hexose transporter activity, e.g., HXT9 or HXT11 activity. An "independently regulated" hexose transporter gene refers to a hexose transporter gene that is operably linked to a regulatory control element which is not under the control of the PDR that controls its expression from its native promoter. For example, an "independently regulated" HXT9 gene is regulated in a PDR1-independent manner, and an "independently regulated" HXT11 gene is regulated in a PDR3-independent manner. In a preferred embodiment, as indicated in the strategy outlined above, the expression of HXT genes are regulated by placing HXT gene sequences under the control of an inducible promoter. In this way, the expression of HXT9 and HXT11 can be modulated to optimize for uptake of particular small molecule therapeutic candidates of interest. A wide range of expression levels can be obtained by utilizing a variety of inducible regulatory sequences. Levels of expression from expression constructs can also be varied by using promoters of different strengths. A number of such promoters are available for recombinant gene expression in yeast (Struhl, "Yeast Promoters" in Maximizing Gene Expression, Reznikoff and Gold (eds.), Butterworth Publishers, 1986; Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology (eds.), Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology (eds.), Berger & Kimmel, Acad. Press, N.Y., Vol. 152, pp. 673–684; and The Molecular Biology of the Yeast Saccharomyces, 1982, Strathern et al. (eds.) Cold Spring Harbor Press, Vols. I and II). For example, a HXT gene can be operably linked to yeast promoter sequences such as, but not limited to, cycl (Guarente et al., 1984, Cell 36:503–511); gal1,10 (West et al., 1984, Mol. Cell. Biol. 4:2467–2478; Giniger et al., 1985, Cell 40:767–774); his3 (Struhl 1982, 1985, Cold Spring Harbor Symp. Quant. Biol. 47:901–910); his4 (Donahue et al., 1983, Cell: 32:89–98), leu2 (Martinez-Arias and Casadaban, 1984, Nature 307:740–742); or matα (Siliciano and Tatchell, 1984, Cell 37:969–978), which are typically inducible by providing specific transcription factors in trans. Levels of expression from expression constructs can also be varied by using regulatory sequences of different strengths.

In another embodiment, promoter sequences from a heterologous, non-yeast gene can be utilized to yield inducible, high levels of expression of genes conferring permeability. For example, in one embodiment, E. coli lacOP regulatory sequences can be operably linked to nucleotide sequences encoding a hexose transporter in a yeast cell that also carries the E. coli lacI gene. Expression from lac operator sequences can then be induced, for example, using the gratuitous inducer IPTG. Other heterologous inducible expression systems that can be utilized include but are not limited to, the araC regulatory region which is inducible by arabinose (AraC), the TET system (Geissendorfer and Hillen, 1990, Appl. Microbiol. Biotechnol. 33:657–663), the $P_L$ promoter of phage λ temperature and the inducible lambda repressor $CI_{857}$ (Pirrotta, 1975, Nature 254: 114–117; Petrenko et al., 1989, Gene 78:85–91), the trp promoter and trp repressor system (Bennett et al., 1976, Proc. Natl. Acad. Sci. USA 73:2351–55; Warne et al., 1986, Gene 46:103–112), the lacUV5 promoter (Gilbert and Maxam, 1973, Proc. Natl. Acad. Sci. USA 70:1559–63), lpp (Nokamura et al., et al., 1982, J. Mol. Appl. Gen. 1:289–299), phoA (alkaline phosphatase), recA (Horii et al. 1980), and the tac promoter, a trp-lac fusion regulatory region, which is inducible by tryptophan (Amann et al., 1983, Gene 25:167–78). Such regulatory regions can all be used in yeast by providing trans-acting repressor proteins in trans. Sequences of such regulatory regions and trans-acting factors are available from Genbank; Burks et al., 1991, Nucl. Acids Res. 19:2227–2230).

The inserted recombinant hexose transporter gene can also comprise nucleotide sequences for protein expression, or manipulation or maintenance of the inserted DNA. For example, transcription, RNA processing, translation, and/or termination signals may be included, in the appropriate position in the vector. The efficiency of expression may be enhanced by the inclusion of appropriate transcription enhancer elements, transcription terminators, etc. (see Bittner et al., 1987, Methods in Enzymol. 153:516–544). Such elements may include, but are not limited to promoter sequences (e.g., TATA boxes, CAT boxes, transcription factor recognition sites), enhancer sequences such as upstream activation elements, and termination signals. Specific initiation signals may also be required for efficient translation of inserted hexose transporter coding sequences. These signals include the ATG initiation codon and adjacent sequences, such as ribosome binding sites and Kozak consensus sequences. In cases where the entire hexose transporter gene, including its own initiation codon and adjacent sequences, is inserted into the appropriate expression vector, no additional translational control signals may be needed. However, in cases where only a portion of the hexose transporter coding sequence is inserted, exogenous translational control signals, including the ATG initiation codon, must be provided. Furthermore, the initiation codon must be in phase with the reading frame of the hexose transporter coding sequence to ensure translation of the entire insert. These exogenous transcription and translational control signals and initiation codons can be of a variety of origins, both natural and synthetic.

In a preferred embodiment, a reporter gene encoding a selectable marker required for growth on a specific substrate is used to select for recombinants. The reporter gene can be a gene that encodes any protein capable of conferring a detectable or a selectable trait on a yeast cell in which it is expressed. Examples of suitable markers are well known in the art. Typically, a prototrophic marker gene is used to confer the ability to grow under selective conditions, allowing positive growth selection for recombinants. An example of such a selectable marker is the URA3 gene, which allows growth on media containing uracil. Other types of selectable markers are also possible. For example, such selectable markers include, but not limited to, the LEU2 gene, whose product confers growth on media lacking leucine, or LYS2, whose product can be selected for by growth on media without lysine. Other non-limiting examples of reporter genes include a variety of genes encoding reporters well known to those of skill in the art, including enzymatic bioluminescent, chemiluminescent and fluorescent proteins, or proteins that confer antibiotic resistance. For more examples of such selectable markers, see examples of reporter genes described in Section 5.2, below.

Cells which can be used for construction of the novel hyperpermeable yeast cells of the invention are any yeast cells that allow selection of the reporter genes used in the assay. In one embodiment, for example the cells have a disrupted URA3 gene, so that URA3 marker selection is possible. In a preferred embodiment, the yeast cells also provide a background useful for screening for compounds, such as small molecules. In another embodiment, for example, the yeast cell background includes a chromosomal copy of a selectable marker operably linked to a conditionally regulated (e.g., inducible) promoter. In a specific embodiment, the yeast LEU2 gene is provided, operably linked to and under the control of a lexA operator (lexAop-LEU2). In another specific embodiment, the yeast LYS2 gene is provided, operator linked and under the control of a lambda repressor control region (clop-LYS2). Appropriate yeast cells and strains include, but are not limited to, species of the genera Saccharomyces, Schizosaccharomyces, Kluyveromyces, Pichia, Hansenula, or Candida, preferably *Saccharomyces cerevisiae* or *Schizosaccharomyces pombe*. Such yeast cells may be constructed using the methods described herein and techniques well known in the art. Starting cells for producing yeast cell-based systems of the invention can be obtained from commercial sources, private laboratories, or publicly available collections, such as ATCC. It is to be understood that the yeast cells described herein could be constructed and maintained as either haploid or diploid yeast cells. In a preferred embodiment, for example, construction of the hyperpermeable yeast cells and strains is performed using a haploid yeast strain, such that replacement of only a single allele of PDR is necessary. However, for species which lack a sexual cycle and are fixed in the diploid state, e.g., *Candida albicans*, genetic manipulations are carried out in the diploid state by replacement of both alleles.

Standard techniques can be utilized for manipulation and maintaining yeast cells. Standard techniques can also be utilized for recombinant expression, including regulatable expression, can also be utilized (see, e.g., Kaiser, C., 1994, "Methods in Yeast Genetics," Cold Spring Harbor Laboratory Press, New York; Spenser, 1989, "Yeast Genetics," Springer-Verlag, New York; and Sherman et al., 1986, "Methods in Yeast Genetics", Cold Spring Harbor Laboratory, Cold Spring Harbor, New York, each of which is incorporated herein by reference in its entirety). Strains and techniques for genetic manipulation of in *Candida albicans* have also been described and are readily available (Pla et al., 1996 Yeast 12:1677–1702; Fonzi and Irwin, 1993, Genetics 134:717–728).

5.2 Methods for Yeast-Based Screening Assays

The methods of the invention include methods designed for the use of the hyperpermeable yeast cells described in Section 5.1 in screening for candidate therapeutic compounds in a variety of whole cell screening assays. Screening assays may be designed to identify compounds that modulate the activity of a particular gene, gene product, or macromolecular process of interest. For example, such activities include, but are not limited to, signal transduction, protein-protein interaction, translation, or any other desired cellular activity.

Typically, such assays generally involve the steps of: 1) contacting the yeast cell with a test compound; 2) measuring an activity of a gene or a reporter gene, gene or reporter gene product, or cellular process of interest; and 3) comparing the level of such activity in the presence of the test compound to the level of activity in the absence of the test compound, such that if the level of activity in the presence of the test compound differs from the level of activity in the absence of the test compound, then a compound that modulates the activity is identified. As used herein, measuring the "activity" of a gene or a reporter gene of interest encompasses measuring the level of transcription, the amount of gene product or reporter gene product, or an activity of the gene or gene product, i.e. enzymatic, immunogenetic, binding activity, etc.

In one embodiment, for example, the hyperpermeable yeast cells can be used to screen test compounds to identify a compound that modulates the activity or expression of a gene of interest by measuring a change in expression of the gene of interest upon contacting the hyperpermeable yeast cell with a test compound. In another embodiment, the hyperpermeable yeast cells can be used to screen test compounds to identify a compound that modulates the activity of a protein of interest by measuring a change in protein activity upon contacting the hyperpermeable yeast cells with a test compound.

In various embodiments, the gene of interest may be a heterologous gene e.g., a mammalian gene, expressed on an extrachromosomal replicon or, alternatively, integrated into the yeast chromosome. Furthermore, the activity or expression of a gene, gene product, or macromolecular process may be measured directly or indirectly. For example, gene expression may be measured by assaying the levels of a gene product, such as an RNA transcript or a protein. Alternatively, expression may be measured indirectly, for example, by the use of a reporter gene that is under the control of, or in some other way responds to, the expression of the gene of interest.

In particular, the hyperpermeable yeast cells are well-suited for yeast two-hybrid screens designed to identify compounds that modulate macromolecular interactions, e.g., protein-protein interactions. The yeast two-hybrid screening assay is a well-known system developed for the study of protein-protein interactions in yeast and for the identification of their corresponding genes (Fields and Song, 1989, Nature 340:245–246; U.S. Pat. No. 5,468,614; White, 1996, Proc. Natl. Acad. Sci. USA 93:10001–10003; Warbick, 1997, Structure 5:13–17). In the classic version of the yeast two-hybrid system, a target protein of interest (X) and its binding partner (Y) are expressed in a yeast cell, wherein each component is fused to either a DNA-binding domain (DB) or a transcriptional activation domain (AD). Also present in the cell is a reporter gene encoding a detectable marker, under the control of a promoter containing one or more DB binding sites. Upon interaction between amino acid sequences of DB-X with amino acid sequences of AD-Y, a transcriptionally active complex (DB-X:AD-Y) is formed, resulting in activation of reporter gene expression. In this way, yeast cell colonies expressing DB-X:AD-Y-interacting macromolecules can be identified, for example, by detecting the detectable marker (Gyris et al., 1993, Cell 75:791–803; Durfee et al., 1993, Genes Dev. 7:555–569; Vojtek et al., 1993, Cell 74:205–214).

For a non-limiting approach according to the present invention, such a system can comprise a modified hyperpermeable yeast cell, comprising the following:
(1) a first fusion gene comprising a nucleotide sequence that encodes a DB operatively linked to a nucleotide sequence encoding a partner protein of interest (or a portion thereof involved in the protein-protein interaction of interest) for which an interaction has been previously established;
(2) a second fusion gene comprising a nucleotide sequence that encodes a transcriptional activation domain protein operatively linked to a target protein (or a portion thereof involved in the protein-protein interaction of interest) of the partner protein of (1); and
(3) a reporter gene linked to a DB binding site.

Components (1), (2), and (3) are introduced in a cell of the hyperpermeable yeast strain, for example, integrated into the chromosome, or introduced into the cell on one or more extrachromosomal replicons by any of a variety of method known in the art. The cell is incubated under conditions whereby the first and the second fusion genes are expressed (either constitutively or in a regulated, e.g., inducible, manner), and the level of reporter gene activity is measured in the presence of a test compound. The level of reporter gene activity is then compared to the level of reporter gene activity in the absence of the test compound. If the level of activity in the presence of the test compound differs from the level of activity in the absence of the test compound, then the test compound is identified as a candidate compound that can be used to target the particular protein-protein interaction. Such a compound is selected for further analysis, such as testing in mammalian cells for its ability to act as therapeutic compound.

In a specific embodiment of the invention, a novel dual bait two-hybrid assay is used to selectively identify modulators of interacting macromolecules. The dual-bait system described herein provides a highly sensitive system for yeast two-hybrid screening using a dual-bait reporter system which allows discrimination between specific and non-specific interactions. The system allows first, detection of a particular target-partner macromolecular interaction, e.g., a protein-protein interaction, and second, in the same cell, identification of compounds that modulate this interaction.

One embodiment of such an internally controlled yeast two hybrid scheme is depicted in FIG. 16A. This system comprises: first, a target protein (the "bait") fused to a DNA-binding domain (DB), which is depicted as LexA in FIG. 16A; second, a partner protein (the "prey") fused to an activator domain (Act); third, a first DB binding site operatively linked to a first reporter gene, which is depicted as lexAop LEU2 in FIG. 16A; and fourth, a first DB binding site operatively linked to a second reporter gene, which is depicted as lexAop lacZ in FIG. 16A. Thus, interaction between target and partner protein in this system results in activation of both reporter genes, allowing two distinct measurements of target-partner interaction. This is particularly advantageous in screening assays for compounds that interfere with such interactions. When the cell is contacted with a test compound that interferes with the interaction of the target protein and the partner protein, both reporter genes will be de-activated. Thus, having two distinct measurements of the target-partner interaction using two different reporter genes reduces the number of "false positives" selected in an a particular screen. An example of such as screen is described in detail in Section 7, below.

Another embodiment, a dual-bait system two-hybrid screening system, is depicted in FIG. 16B. This system adds additional plasmids which can provide negative controls to further reduce the number of false positive candidate test compounds selected in a particular screen. The system comprises a yeast two-hybrid system with three additional components compared to the yeast two-hybrid two-reporter system depicted in FIG. 16A. First, an alternative target protein ("Bait 2" in FIG. 16B) is fused to a second DNA binding domain ($DB_2$), depicted as cI in FIG. 16B; second, a first $DB_2$ binding site is operatively linked to third reporter gene, which is depicted as clop gusA in FIG. 16B; and third, a second $DB_2$ binding site is operatively linked to fourth reporter gene, which is depicted as clop LYS2 in FIG. 16B.

The alternative target fusion protein ("Bait 2") can provide an internal control for identification of non-specific interactions. Upon interaction of the target with a partner, $AD/DB_1$ activates RNA polymerase-dependent transcription from both respective binding sites within their respective reporter constructs, thereby inducing reporter gene expression. In this manner, reporter expression is measured to determine the level of functional $AD/DB_1$ and $AD/DB_2$ interaction. Thus, the presence of two reporter genes in a single cell, each independently responsive to activation by target-partner interaction, offers the opportunity to perform two simultaneous, internally controlled, yet independent screens in a single colony of yeast cells. An example of such as screen is described in detail in Section 7, below.

The alternative target protein, in one embodiment, may be any protein, or portion thereof, that is not expected to interact with the partner protein, thereby serving as a negative control for true interactors. In a preferred embodiment, the alternative target protein is a closely related protein, preferably a member of the same family or proteins, as long as the alternative target is not expected to interact with the partner protein.

In a preferred embodiment, a yeast cell used for the dual-bait screening assay comprises: i) a target protein fused to a first DNA binding domain ($DB_1$); ii) an alternative partner protein fused to a second DNA binding domain; iii) partner protein fused to an activating domain; iv) a first reporter gene operably linked to a first $DB_1$ binding site; v) a second reporter gene operably linked to a second $DB_1$ binding site; vi) a third reporter gene operably linked to a first $DB_2$ binding site; and v) a fourth reporter gene operably linked to a second $DB_2$ binding site.

To identify a candidate test compound that modulates the interaction of a target protein and a partner protein, the cell described above is contacted with a test compound. Next, cells are plated on non-selective and selective media, in the presence and absence of test compound, to detect the activities of the first, second, third, and fourth reporter genes. By comparing growth on selective and non-selective media, the levels of activity of the first, second, third, and fourth reporter genes are compared to the levels of the first, second, third, and fourth reporter gene, respectively, obtained in the absence of said test compound. If the levels of activity of the first and second reporter genes differs from the levels obtained in the absence of the test compound, a candidate test compound that modulates the interaction of the target protein and the partner is identified. If the levels of the third and fourth reporter genes do not significantly differ from the levels obtained in the absence of test compound, then the identified candidate test compound is likely to be specific to the target protein-partner protein interaction. Thus, a test compound that decreases activity from the first and second reporters relative to their activity in the absence of test compound, but does not affect the relative activity of the third and fourth reporter genes is selected as a candidate compound that specifically interferes with target-partner interaction. A candidate test compound identified in this assay can then be tested further, for example, in assays designed to test the activity of such a compound in mammalian cells.

The above outlined approach, therefore provides a yeast-based strategy to identify a test compound that will block a protein-protein interaction of interest and thereby identify potential therapeutic compounds.

Any reporter gene sequence may be utilized for the dual bait two hybrid system described herein. The activities of the products of the reporter gene sequences of (1) and (2) must be distinguishable from each other. The reporter gene can be a gene that encodes any protein capable of conferring a detectable or a selectable trait on a yeast cell in which it is expressed, for example, growth under a particular condition. In a preferred embodiment, the reporter gene is a prototrophic reporter gene, which confers the ability to grow under selective conditions. In various embodiments, auxotrophic or prototrophic reporter genes are used, including, but not limited to, the LEU2 gene, whose product is required for growth on media lacking leucine, LYS2, whose product can be selected for by growth on media without lysine, HIS3 whose product can be selected for by growth on media without histidine, or TRP3, whose product is required for growth on media lacking tryptophan. Other types of reporter genes are also possible. Non-limiting examples of reporter genes include a variety of genes encoding reporters well known to those of skill in the art, including enzymatic bioluminescent, chemiluminescent and fluorescent proteins, or proteins that confer antibiotic resistance. Such reporters include, but are not limited to β-galactosidase (Nolan et al. 1988, Proc. Natl. Acad. Sci. USA 85:2603–07), β-glucuronidase (Roberts et al. 1989, Curr. Genet. 15:177–180), luciferase (Miyamoto et al., 1987, J. Bacteriol. 169:247–253), β-lactamase conferring ampicillin resistance, chloramphenicol transacetylase (CAT), conferring chloramphenicol resistance, and gene sequences encoding polypeptides which confer zeocin resistance (Hegedus et al. 1998, Gene 207:241–249) or kanamycin resistance (Friedrich and Soriano, 1991, Genes. Dev. 5:1513–1523). In one specific example, a reporter gene sequence comprises a nucleotide sequence which encodes a LacZ gene product, β-galactosidase. The enzyme is very stable and has a broad specificity so as to allow the use of different histochemical, chromogenic or fluorogenic substrates, such as, but not limited to, 5-bromo-4-chloro-3-indoyl-β-D-galactoside (X-gal), chlorophenol red β-D-galactoside (CPRG, Eustice, et al, 1991, Biotechniques 11: 739–742), lactose 2,3,5-triphenyl-2H-tetrazolium (lactose-tetrazolium), and fluorescein galactopyranoside (Nolan et al. 1988, Proc. Natl. Acad. Sci. USA 85:2603–07).

The transcriptional activation domain can be any protein, or domain or fragment thereof, capable of activating transcription in yeast when functionally associated with a DNA binding domain. In one embodiment, the transcriptional activator is comprised of a GAL4 activation domain. In another embodiment, the transcriptional activator is comprised of a GCN4 activation domain.

The DNA binding domain can be any protein, or domain or fragment thereof, natural or artificial, capable of recognizing and binding to a specific DNA recognition site, including, but not limited to, a Gal 1 DNA-binding domain, a LexA domain, or a cI DNA-binding domain.

Plasmids routinely used in yeast typically contain a selectable marker(s) and sequences for replication and mitotic segregation. These regions are comprised of either an autonomously replicating sequence (ARS) and a centromere or replication and partitioning sequences from the endogenous yeast $2\mu m$ plasmid. The plasmid vector may also contain additional nucleotide sequences of interest for protein expression, manipulation or maintenance of the inserted DNA. For example, transcription, processing, and translation signals may be included, in the appropriate position in the vector. Such elements may include, but are not limited to promoter sequences (e.g., TATA boxes, CAT boxes, transcription factor recognition sites), upstream activation sequences, translation signals (e.g., ribosome binding sites, Kozak consensus sequences) and termination signals.

Plasmids constructs used for construction of yeast two-hybrid dual-bait systems and yeast cells and strains with modified permeability of the invention can be constructed according to standard recombinant DNA techniques (see e.g., Methods in Enzymology, 1987, volume 154, Academic Press; Sambrook et al. 1989, Molecular Cloning—A Laboratory Manual, 2nd Edition, Cold Spring Harbor Press, New York; and Ausubel et al. Current Protocols in Molecular Biology, Greene Publishing Associates and Wiley Interscience, New York, which are incorporated herein in their entirety).

Yeast cells which can be used for the screening assays of the invention can be from any appropriate strain of yeast that allows selection of the reporter genes used in the assay. For example, where LEU2 is used as a reporter gene, the endogenous LEU2 gene is inactivated. Likewise, where LYS2 is used as a reporter gene, a yeast strain is used that has the endogenous LYS2 inactivated. Such prototrophic and auxotrophic mutants may be naturally occurring, or may be engineered by gene disruption methods well known in the art (see Kaiser, 1994, "Methods in Yeast Genetics," Cold Spring Harbor Laboratory Press, New York; and Spenser, 1989, "Yeast Genetics," Springer-Verlag, New York). For vectors suitable for regulated and inducible expression, see Section 5.1, above.

5.3 Compounds for Use in Screening Assays

Compounds that can be tested and identified in the yeast-based screening methods described herein can, in general, include any compounds which, upon exogenous addition to the cells of the invention, can enter the yeast cell membrane. Test compounds can include, but are not limited to, compounds obtained from any commercial source, including Aldrich (1001 West St. Paul Ave., Milwaukee, Wis. 53233), Sigma Chemical (P.O. Box 14508, St. Louis, Mo. 63178), Fluka Chemie AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, La. 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272). Further any kind of natural products may be screened using the methods of the invention, including microbial, fungal or plant extracts.

Furthermore, diversity libraries of test compounds, including small molecule test compounds, may be commercially obtained from Specs and BioSpecs B. V. (Rijswijk, The Netherlands), Chembridge Corporation (San Diego, Calif.), Contract Service Company (Dolgoprudny, Moscow Region, Russia), Comgenex USA Inc. (Princeton, N.J.), Maybridge Chemicals Ltd. (Cornwall PL34 OHW, United Kingdom), and Asinex (Moscow, Russia). Combinatorial libraries of test compounds, including small molecule test compounds, can be may be generated as disclosed in Eichler & Houghten, 1995, Mol. Med. Today 1:174–180; Dolle, 1997, Mol. Divers. 2:223–236; Lam, 1997, Anticancer Drug Des. 12:145–167. These references are incorporated hereby by reference in their entirety. It is to be noted that such references also teach additional screening methods which may be employed for the further testing of compounds identified via the methods of the invention and which can aid in identifying and isolating compounds which can represent leads and therapeutic compounds having a desired effect on the physiological activity and/or function assayed in the yeast-based screening assay.

5.4 Kits

The cells, vectors, and compounds of the invention can be provided in kits. In one embodiment, the invention provides a kit for performing a yeast-based screening assay comprising, in one or more containers, modified hyperpermeable yeast cells. In another embodiment, the modified hyperpermeable yeast cell kit further comprises a DNA vector or vectors for dual-bait two-hybrid screening, and a reporter gene. In another embodiment, the kit can further comprise a library of small molecule therapeutic candidates.

6. EXAMPLE 1

Construction of Hyperpermeable Yeast Strains

The Examples presented in this Section describe, first, the genetic engineering of a strain of the yeast *S. cerevisiae* constructed by inserting HXT9 and HXT11 into the PDR1 and PDR3 loci, respectively. This strain is demonstrated to exhibit increased permeability to exogenously supplied compounds, such as small molecules. Second, described herein is the construction of vectors and cells, and their application in methods for one-step, efficient, and high-throughput screening in yeast.

6.1 Materials and Methods

SKY48 and SKY191 parental strains The parent strains SKY48 and SKY191 (MATαtrp1 URA3 his3 lexAop-LEU2 cIop-LYS2), with 6 or 2 lexA operators upstream of LEU2, respectively, have been described (Serebriiskii et al., 1999, J. Biol. Chem. 274:17080–17087, which is incorporated herein by reference in its entirety).

Figure 3:
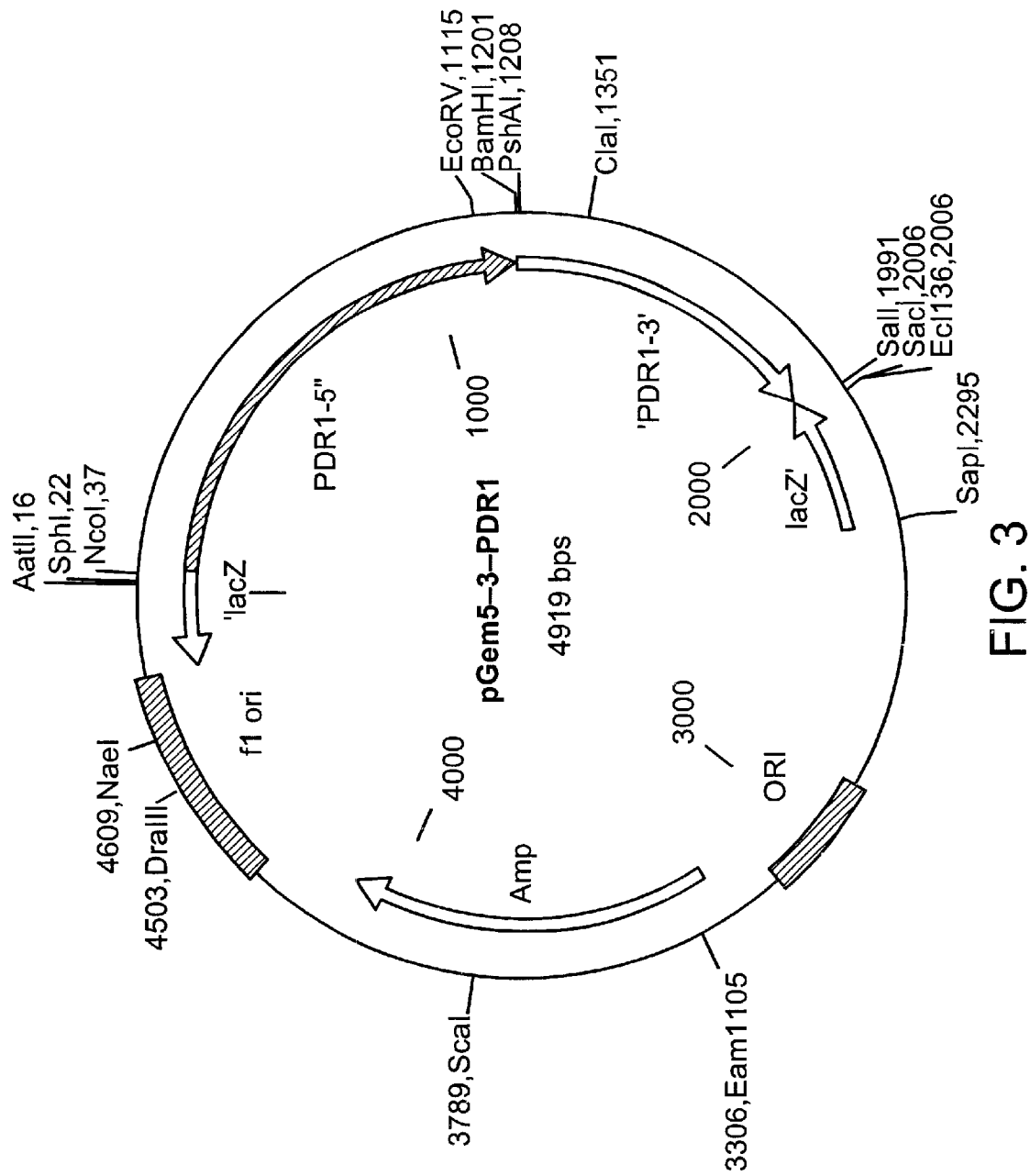
Figure 4:
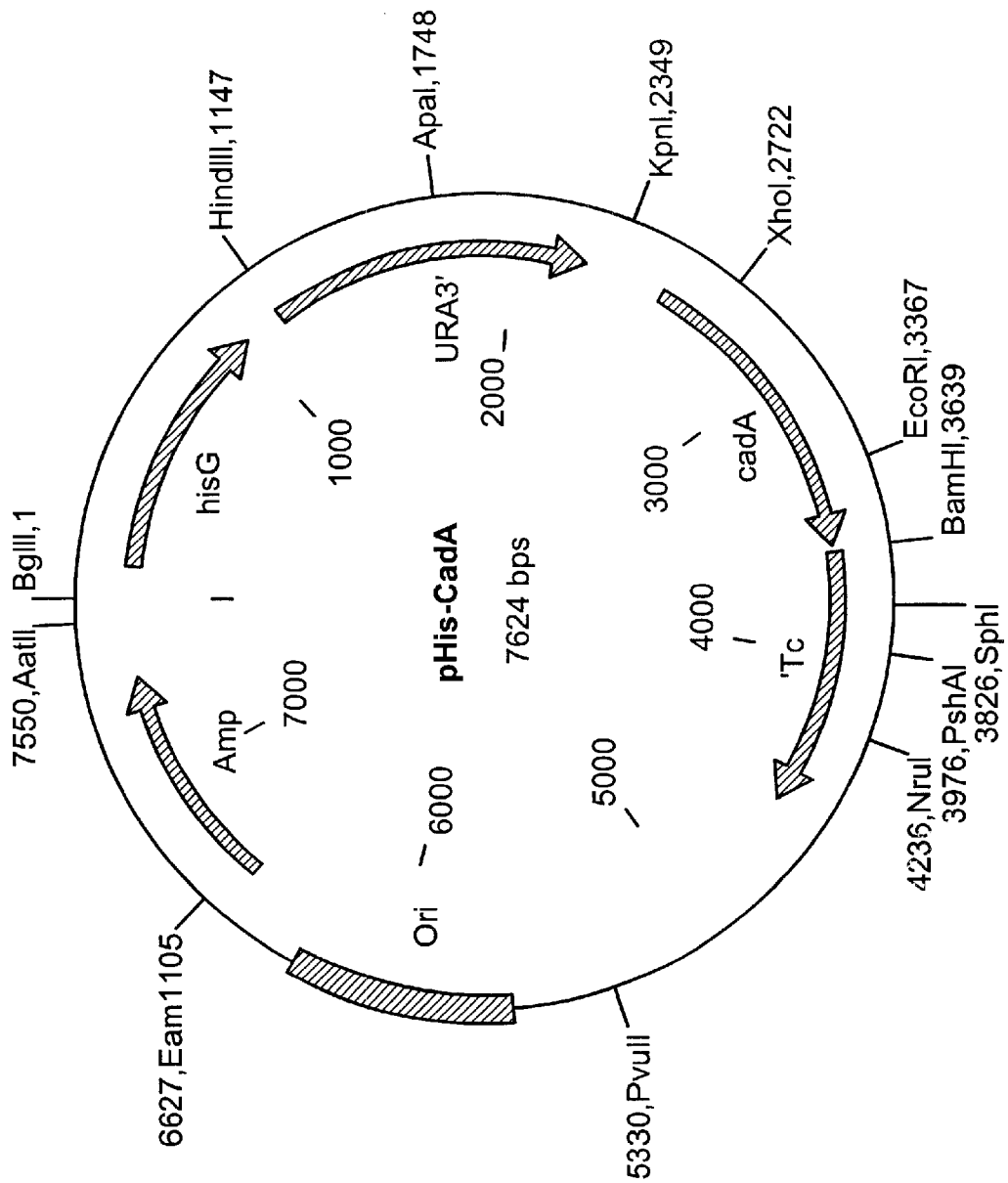
Figure 5:
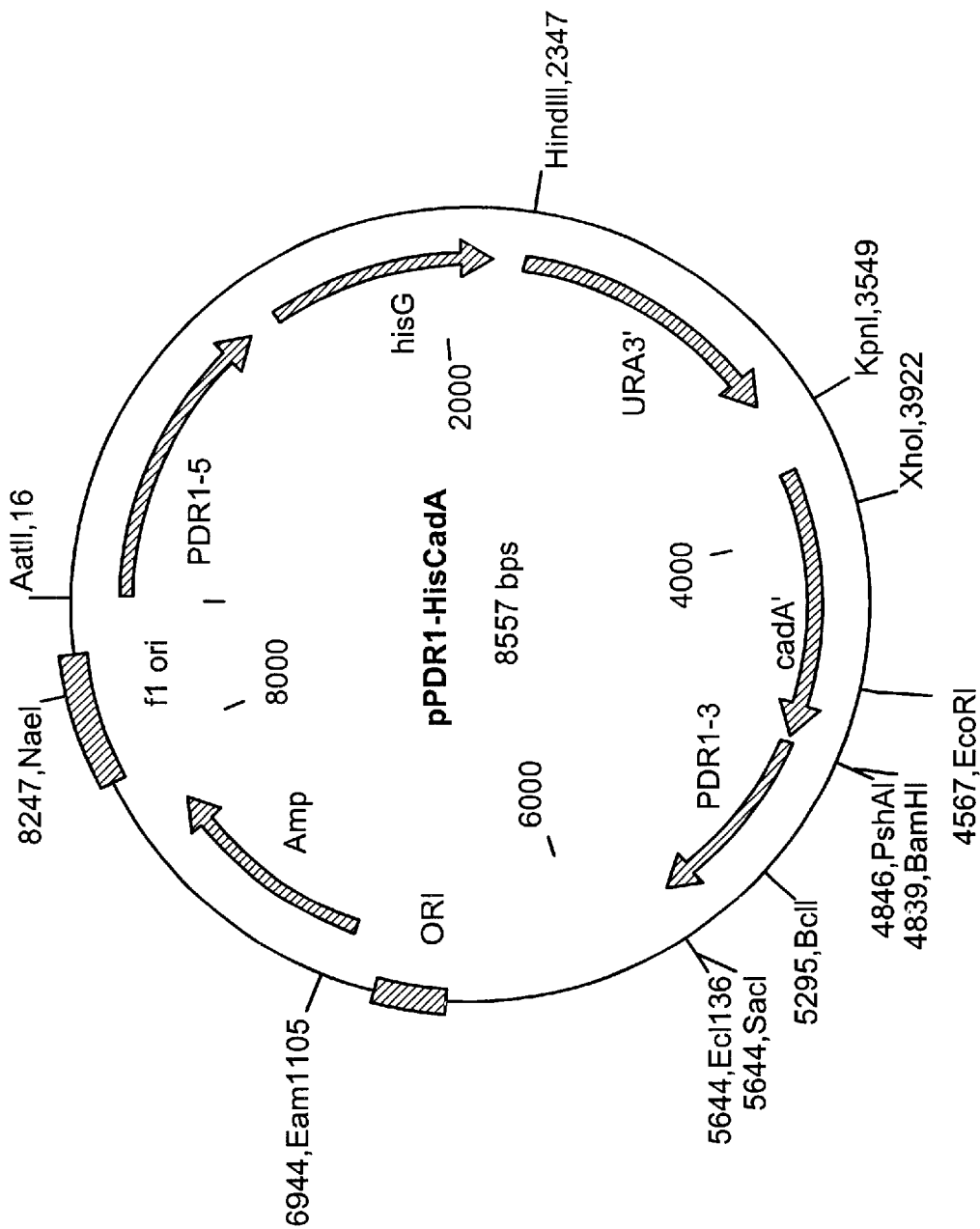

Construction of the pPDR1-HisCadA plasmid Primers VK11 and VK14 (see Table 1) were used to amplify the 1158 base pair (bp) upstream fragment (5' fragment) of PDR1, and primers VK12 and VK13 (see Table 1) were used to amplify the downstream (3' fragment) 741 bp fragment using polymerase chain reaction (PCR). The PDR1 amplified fragments were cloned into pGem-T/A (Promega, Madison, Wis.) to construct the pGem5-3-PDR1 plasmid (FIG. 3) with a unique BamHI site between the fragments. Next, the pHisCadA plasmid (FIG. 4) was constructed by replacing the Salmonella hisG DNA fragment in pNKY51 plasmid with the *E. coli* cadBA gene operon. Next, the hisG-URA3-cadA gene fragment from pHis-CadA was isolated, purified, and ligated into pGem5-3-PDR1 vector to construct the pPDR1-HisCadA plasmid (FIG. 5).

Figure 6:
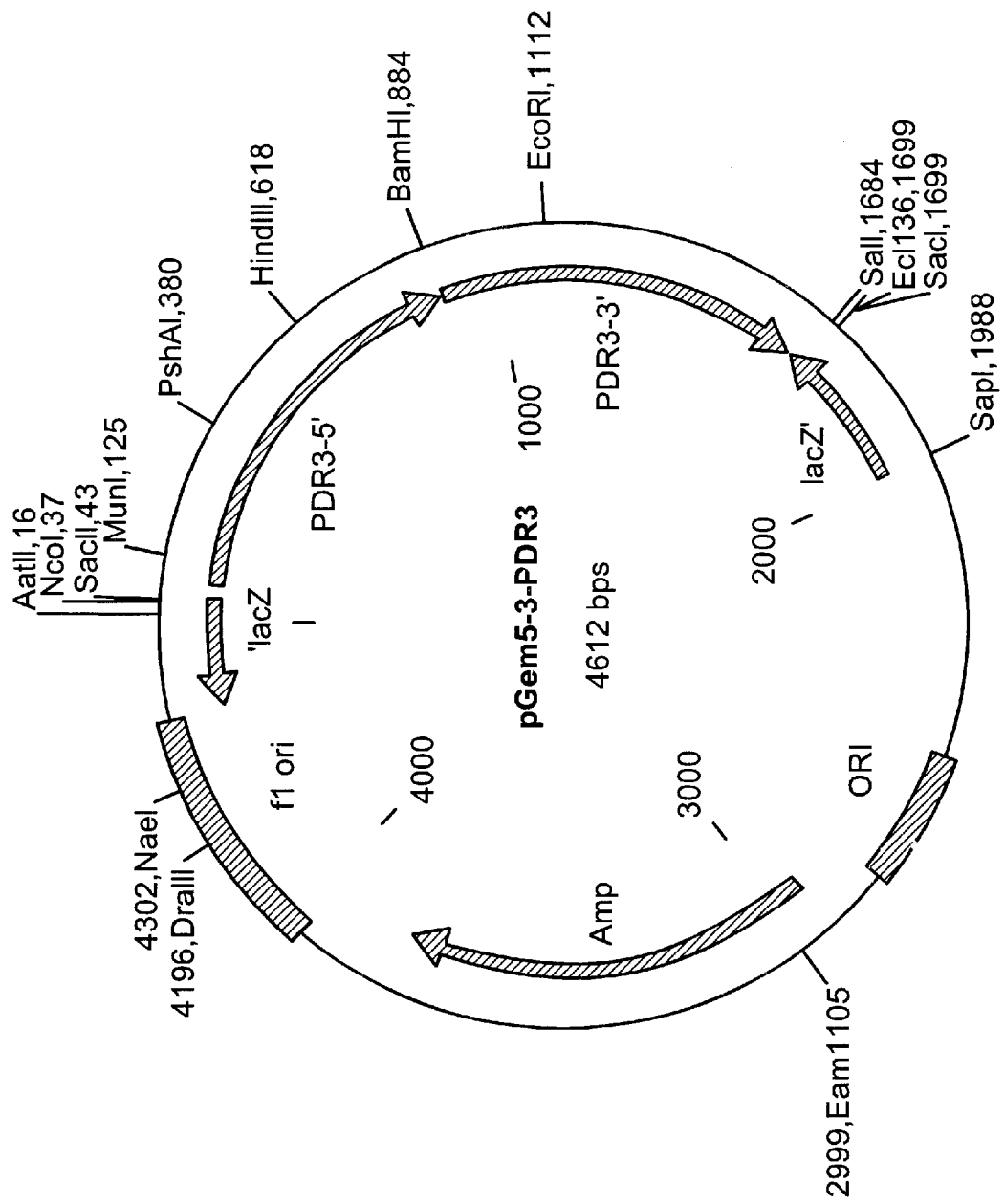
Figure 7:
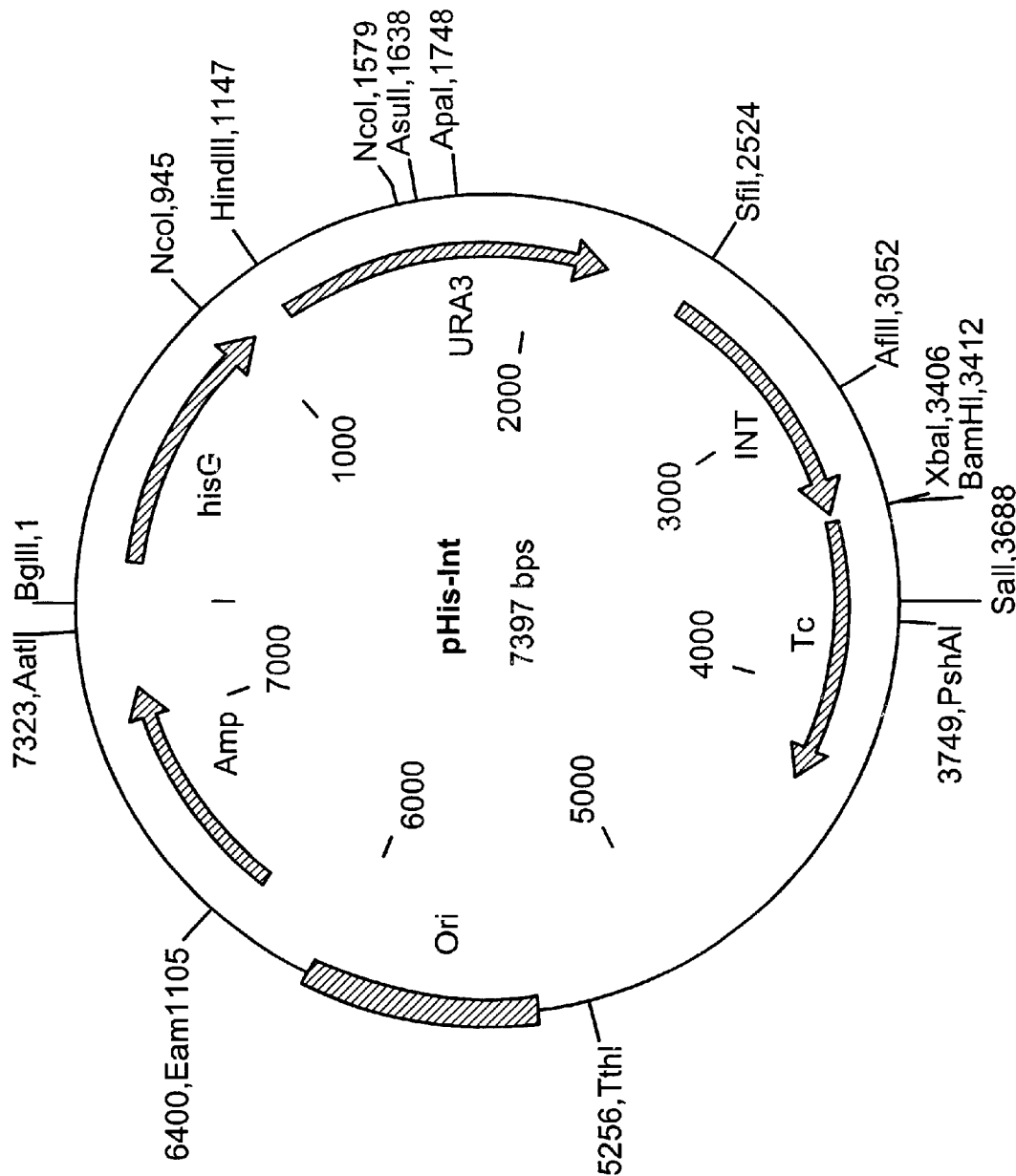
Figure 8:
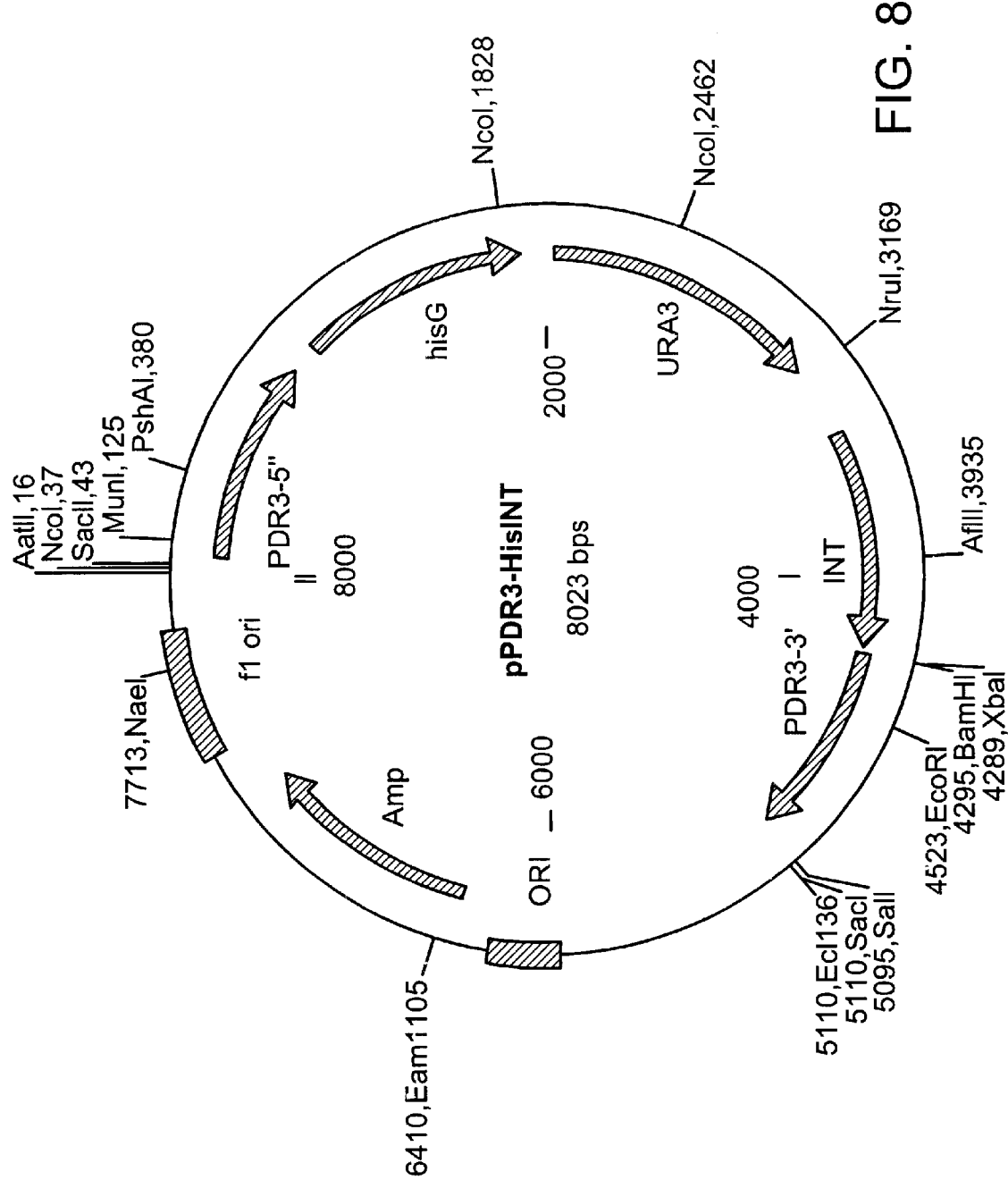

Construction of the pPDR3-HisInt plasmid Primers VK07 and VK10 were used to amplify the 839 bp 5' fragment of the yeast PDR3 gene, and VK09 and VK11 were used to amplify the 743 bp 3' fragment of the yeast PDR3 gene (see Table 1 for sequences of primers). The amplified fragments were then cloned into pGem-T/A (Promega) to create pGEM5-3-PDR3 (FIG. 6), which bears a unique BamHI site between the PDR3 fragments. The pHisInt plasmid (FIG. 7) was then constructed by replacing the hisG 3' fragment of the pNKK51 plasmid (obtained from Alan Hinnebusch, NIH, NICHD, LEGR) with a fragment from the human immunodeficiency virus (HIV) integrase gene (Int). The hisG-URA3-Int fragment was then isolated, purified, and ligated into pGem5-3-PDR3 vector to create the pPDR3-HisInt plasmid (FIG. 8).

Figure 9:
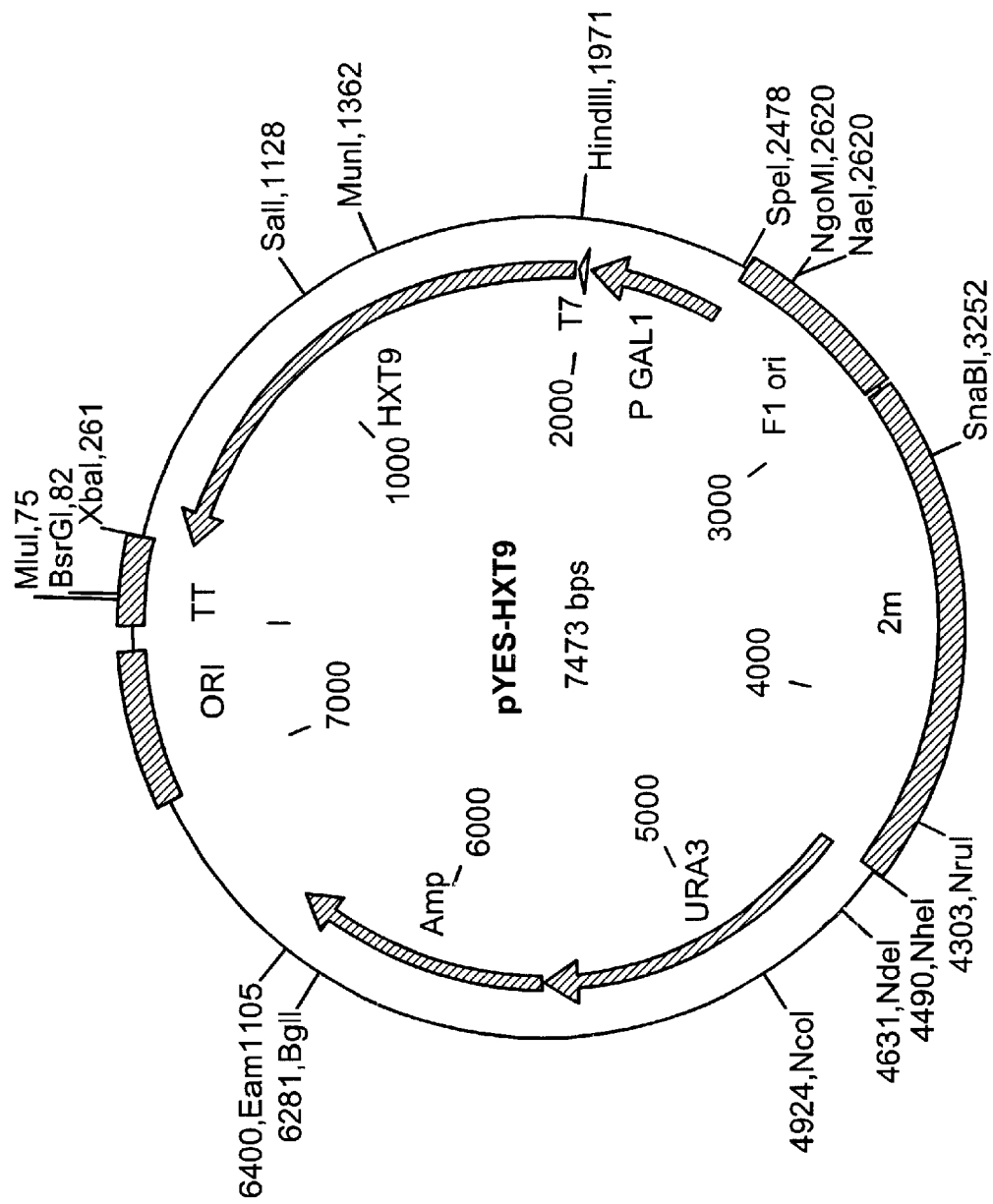
Figure 10:
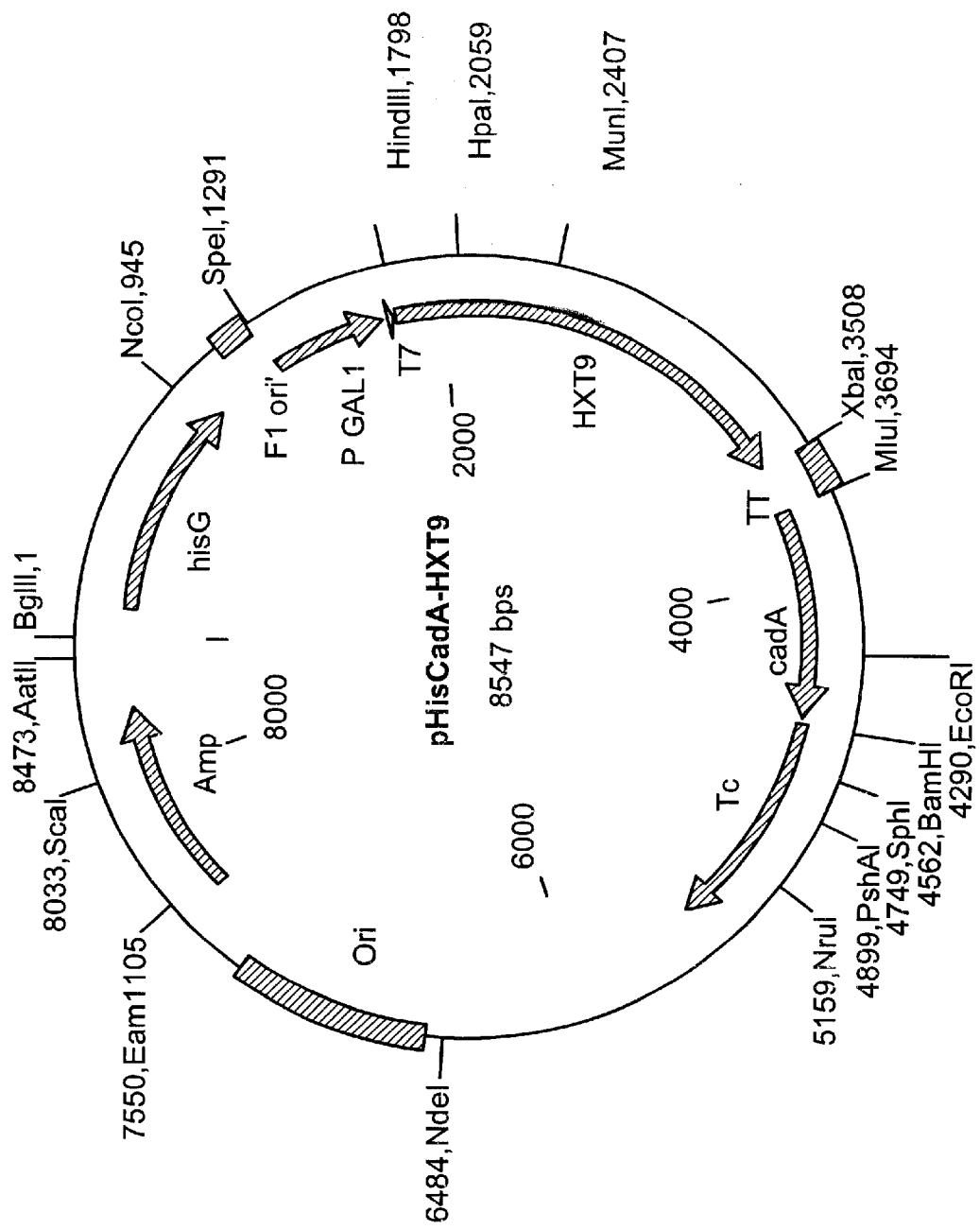

Construction of the pHisCadA-HXT9 plasmid Primers VK05 and VK06 (see Table 1) were used to PCR amplify the coding sequence of the yeast HXT9 gene. The HXT9 gene fragment was ligated downstream of the galactose-1 gene (gal1) inducible promoter and upstream of the CYC transcription terminator region in pYes2 plasmid to create the pYes-HXT9 plasmid (FIG. 9). The fragment containing the gal1 promoter region, the HXT9 gene fragment, and the CYC TT region from pYes-HXT9 were then ligated into pHisCadA (see above) to create pHisCadA-HXT9 (FIG. 10).

TABLE 1

Oligonucletide Primers used in Plasmid and Strain Construction

| Primer | Sequence (5'→3') | | Description |
|---|---|---|---|
| VK03 | CTCAAGCTTATGTCAGGTGTTAATAATACATCC | (SEQ ID NO: 1) | Forward HXT11 |
| VK04 | CCGAAAACTTCTAGATCAGCTGGAAAAG | (SEQ ID NO:2) | Reverse HXT11 |
| VK05 | CTTACCCAAGCTTATGTCCGGTGTTAAT | (SEQ ID NO:3) | Forward HXT9 |
| VK06 | ACCTCTAGATTAGCTGGAAAAGAACCTC | (SEQ ID NO:4) | Reverse HXT9 |
| VK07 | TTAATTTTTTCTTATTGCGTGACCG | (SEQ ID NO:5) | Forward PDR3 |
| VK08 | TGGTTATGCTCTGCTTCCCTATTTC | (SEQ ID NO:6) | Reverse PDR3 |
| VK09 | AAAGGATCCTTTTATGTGGAAGACCCGCA | (SEQ ID NO:7) | Forward PDR3 from 2188 bp |
| VK10 | TTTGGATCCATTAACATCGATGAACCCGTGT | (SEQ ID NO:8) | Reverse PDR3 from 839 bp |
| VK11 | CAGAAAAGAATCCAAGAAACTGGAAG | (SEQ ID NO:9) | Forward PDR1 |
| VK12 | GAGAACTTTTATCTATACAAACGTATACG | (SEQ ID NO:10) | Reverse PDR1 |

TABLE 1-continued

Oligonucletide Primers used in Plasmid and Strain Construction

| Primer | Sequence (5'→3') | Description |
|---|---|---|
| VK13 | TTTGGATCCTGACAATCGTCACTCG (SEQ ID NO:11) | Forward PDR1 from 2466 bp |
| VK14 | TTAGGATCCTCACAAAGGGCTGCGGTA (SEQ ID NO:12) | Reverse PDR1 from 1158 bp |
| VK15 | GGAAGAATTATTTCTGGCCTAGG (SEQ ID NO:13) | Forward HXT9 and HXT11 from 505 bp |
| VK16 | AATAGACACGTACGGCGTCC (SEQ ID NO:14) | Reverse HXT9 and HXT11 from 1161 bp |
| VK23 | GGAAGAGGTTATCGCCCTGC (SEQ ID NO:15) | Forward hisG from 829 bp of HisHXT11INT cassette |
| VK24 | CCCTGCACTGTACCCCCC (SEQ ID NO:16) | Reverse HIVInt from 4093 bp of MisHXT11INT cassette |

Figure 11:
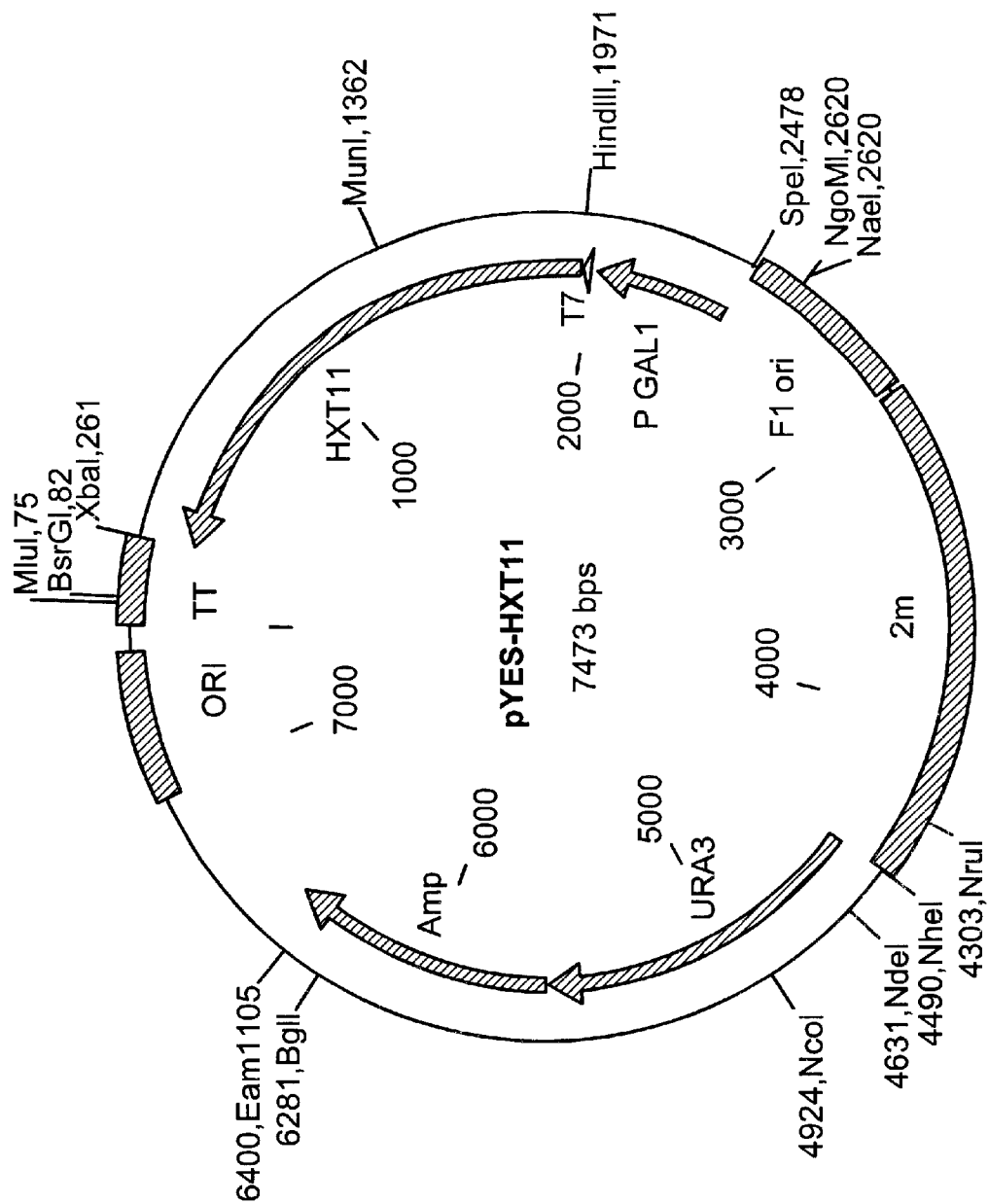
Figure 12:
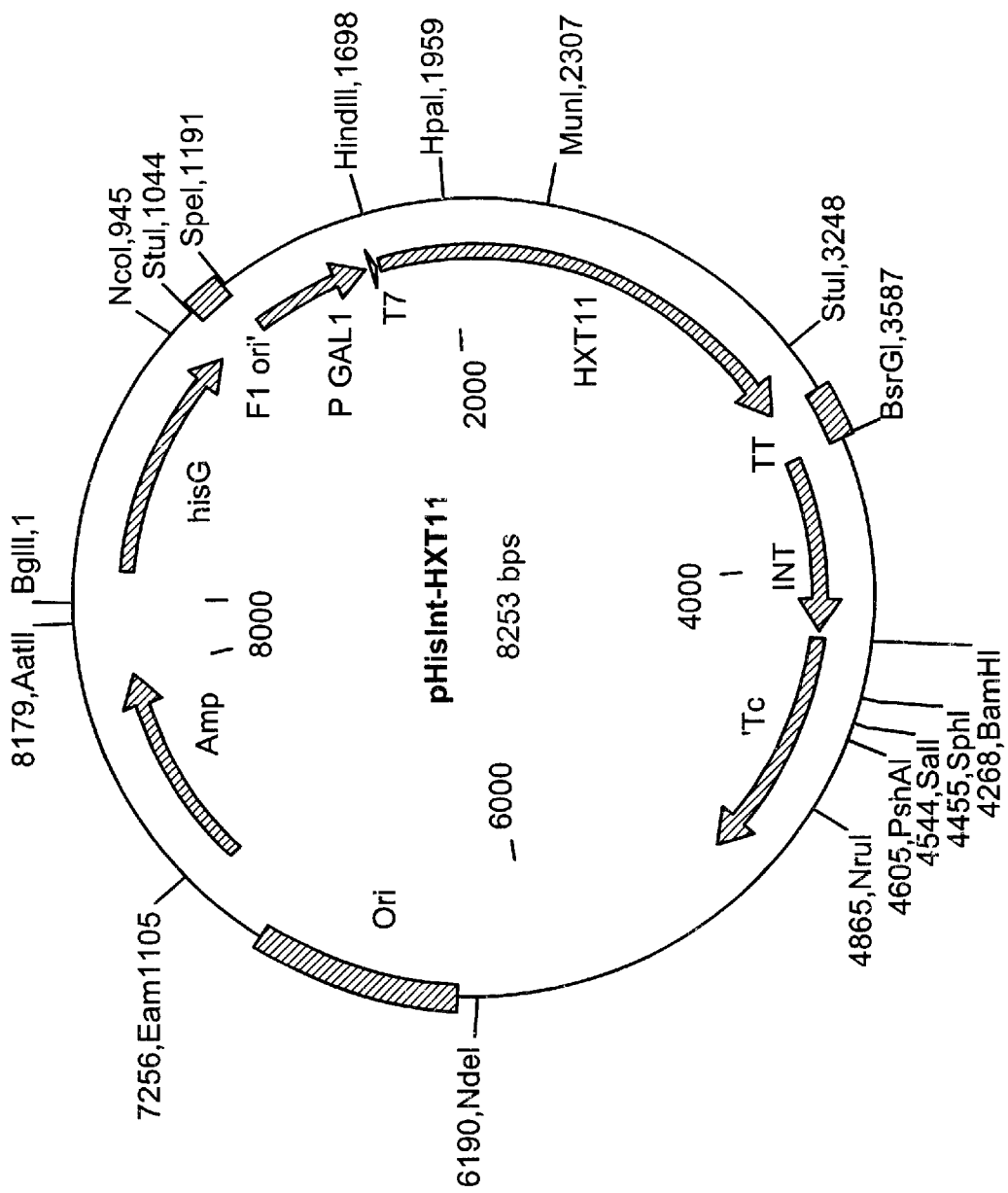

Construction of the pHisInt-HXT11 plasmid Primers VK03 and VK04 (see Table 1) were used to PCR amplify the coding sequence of the yeast HXT11 gene. The HXT11 fragment was ligated downstream of the gal1 inducible promoter and upstream of CYC TT region in the pYes2 plasmid (gift of E. Golemis, FCCC) to create the pYes-HXT11 plasmid (FIG. 11). The fragment containing the Gal1 promoter region, the HXT11 coding region, and the CYC TT region from pYes-HXT11 were then excised, purified, and ligated into pHisInt to create pHisInt-HXT11 (FIG. 12).

Construction of SKY54 and SKY197 Plasmid pPDR3-HisInt was digested with AatII-SacI and the purified integrative cassette, hisG-URA3- PDR3-Int (see FIG. 2C) was transformed into SKY48 and SKY191. Positive cells were selected on yeast dropout media that lacked uracil. Cells that grew on such media contained integrated copies of hisG-URA3-Int cassette and were named SKY49 and SKY192.

Strains SKY49 and SKY192 were used for the next round of integrative transformation. The goal of this transformation was to replace the URA3 gene at the PDR3 locus in the chromosome of SKY49 and SKY192 with a galactose inducible copy of HXT11. To this end, plasmid pHisHXT11Int was digested with AatII and PshAI, and the hisG-HXT11-Int cassette was purified and transformed into SKY49 and SKY192. To select yeast with the hisG-HXT11-Int cassette integrated into the chromosome, cells were propagated on YPD plates for 5–6 hours to decrease the amount of ura3 enzyme, and then replica plated on plates containing minimal DO media containing 1.5 mg/ml 5-Fluoroorotic acid (5FOA) and uracil at a concentration of 1.2 mg/ml. Yeast that express the URA3 gene convert 5FOA to the toxic metabolite and die. However, cells that have replaced the URA3 gene by HXT11 grow normally. Several hundreds of transformants containing the HXT11 gene at the PDR3 chromosomal locus were obtained. Two strains containing the inserted cassettes (FIG. 2C) were selected, named SKY51 and SKY194.

On the next round of integrative transformation, strains SKY51 and SKY194 were transformed with pPDR1-HisCadA. The hisG-URA3-cadA cassette in pPDR1-HisCadA was digested with AatII-SacI and the purified cassette (FIG. 1C) was transformed into SKY51 and SKY194. Two resulting yeast strains, SKY52 and SKY195, were selected on yeast dropout media that lacked uracil. The hisG-HXT9-cadA cassette was then purified and transformed into SKY52 and SKY195, thereby replacing the hisG-URA3-cadA cassette with the hisG-HXT9-cadA cassette. Another round of 5FOA selection (see FIG. 1D) yielded two transformants, SKY54 and SKY197, with HXT9 substituted for URA3 at the PDR1 locus (see FIG. 1E).

Thus, cells selected after this round of integrative transformation have integrated copies of HXT9 and HXT11 at the PDR1 and PDR3 loci, respectively. These strains were named SKY54 (MATαtrp1 ura3 his3 3lexAop-Leu2 1clop-Lys2pdr1::HXT9 pdr3::HXT11) and SKY197 (MAT αtrp1 ura3 his3 1lexAop-Leu2 1clop-Lys2 pdr1::HXT9 pdr3::HXT11).

Unless otherwise defined, all technical and scientific terms used herein have the meaning as commonly understood by one of ordinary skill in the art to which this invention belongs. The practice of the present invention employs, unless otherwise indicated, conventional techniques of chemistry, molecular biology, microbiology, recombinant DNA, and genetics. See, e.g., Sambrook, J. et al. (eds.) 1989. Molecular Cloning: A Laboratory Manual, Cold Spring Harbor Laboratory Press, Cold Spring Harbor, New York; Ausubel et al., (eds.) Current Protocols in Molecular Biology, John Wiley & Sons, New York. 1992; Tuite and Oliver, 1991, Biotechnology Handbooks: Saccharomyces, vol. 4, Plenum Press, New York, which are incorporated by reference in their entirety).

6.2 Results

Figure 13A:
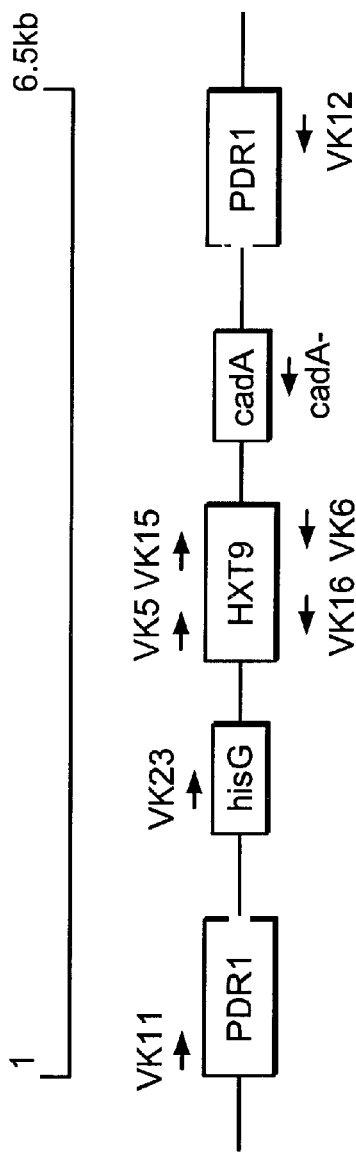
FIG. 13 depicts the structure of the inserted HXT9 gene sequence at the yeast PDR1 locus in strains SKY54-5 and SKY197-1. (A) is a diagram of the structure of the inserted DNA sequence at the PDR1 locus. (B) is an ethidium bromide stained gel of PCR products, confirming the integration of recombinant HXT9 sequences at the PDR1 locus.
Figure 13B:
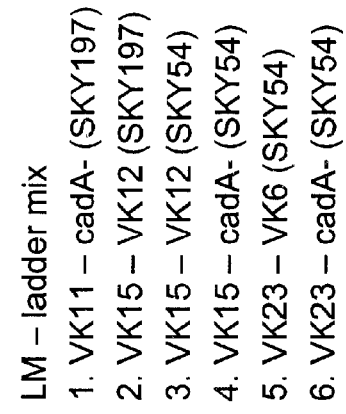
Figure 13B:
Figure 14A:
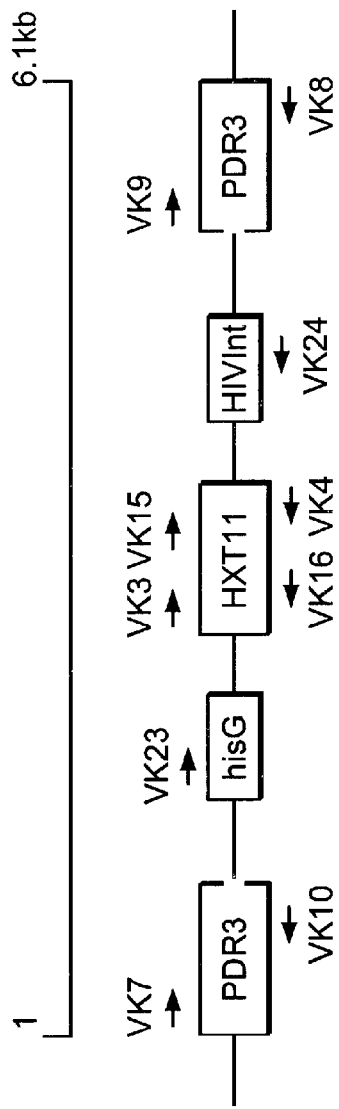
FIG. 14 depicts the structure of the inserted HXT11 DNA sequence at the yeast PDR3 locus in strains SKY54-5 and SKY197-1. (A) is a diagram of the structure of the inserted DNA sequence at the PDR3 locus. (B) is an ethidium bromide stained agarose gel of PCR products, confirming the integration of recombinant HXT11 sequences at the PDR3 locus.
Figure 14B:
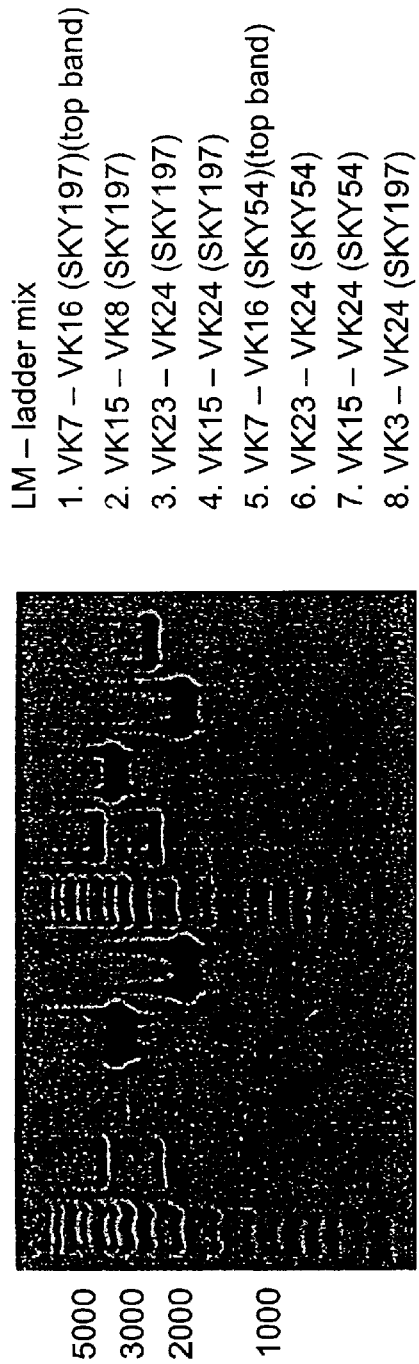

Characterization of SKY54 and SKY197 To confirm the proper insertion of HXT9 and HXT11 into the chromosomal loci of PDR3 and PDR1, respectively, SKY54 and SKY197 genomic DNA was purified and analyzed using PCR for the presence of HXT9 and HXT11 recombinant sequences (FIGS. 13A–B and 14A–B, respectively). FIG. 13A depicts the DNA fragment PDR1-hisG-HXT9-cadA-PDR1, which was inserted into the PDR1 locus of SKY54 and SKY 197, showing the location and orientation of PCR primers. FIG. 13B shows an agarose gel stained with ethidium bromide stained gel to visualize the PCR products. The six bands correspond to the proper lengths between the specific primer pairs and confirm the correct insertion and orientation of the cassettes. FIG. 14A depicts the DNA fragment PDR3-hisG-HXT11-Int-PDR3 that was inserted into the PDR3 locus of SKY54 and SKY197, indicating the location and direction of PCR primers. FIG. 14B shows an Ethidium bromide stained gel of the PCR products. The eight bands correspond to the proper lengths between the specific primer pairs and confirm the correct insertion and orientation of the cassettes.

TABLE 2

Sensitivity of SKY48 AND SKY54 To SMT Combinatorial Chemistry Library

| Strain | # Compounds Tested | # of Hits | % of Hits |
|---|---|---|---|
| SKY48 | 73,400 | 1959 | 2.7 |
| SKY48 | 73,400 | 3011 | 4.1 |

Yeast strain sensitivity to selected compounds SKY54 and SKY197 were tested for sensitivity to various concentrations of compounds, including cycloheximide (CYH), 4-nitroquinolin-oxide (NQO), sulfmethuron methyl (SMM) and Zeocin (Zeo), relative to the sensitivity of the parental strains, SKY48 and SKY191 to these compounds. Yeast cells were propagated on YPD or YPG/R plates in top-agar layer containing 1% of low melt SeaPlaque agarose and YPD or YPG/R growth media with glucose or galactose as the carbon source. CYH (5 mg/ml), NQO (2.5 mg/ml), SMM (100 mg/ml) and Zeo (100 mg/ml) stock solutions were diluted 2, 5, 10, 25, and 100-fold, and applied on top-agar growing yeast by means of prone device. Sensitivity to various concentrations of compounds was scored by visualization of growth on this media, and the size of "death zones" of sensitive colonies. Thus, the plates shown in FIG. 15 show the sensitivity of the parental and modified yeast strains to, from top to bottom of each plate, and from left to right of each row, 5 $\mu$g, 2.5 $\mu$g, 1 $\mu$g, 0.5 $\mu$g, 0.2 $\mu$g, and 50 ng of CYH; 2.5 $\mu$g, 1.25 $\mu$g, 0.5 $\mu$g, 0.25 $\mu$g, 0.1 $\mu$g, and 25 ng of NQO; 100 $\mu$g, 50 $\mu$g, 20 $\mu$g, 10 $\mu$g, 4 $\mu$g, and 1 $\mu$g of SMM; and 100 $\mu$g, 50 $\mu$g, 20 $\mu$g, 10 $\mu$g, 4 $\mu$g, and 1 $\mu$g of Zeo. As shown in FIG. 15, both parental strains SKY48 and SKY191, and modified strains SKY54 and SKY197, showed no sensitivity to SMM at all concentrations tested. However, based on the size of the death zones, SKY54 and SKY197 are significantly more sensitive to the same concentration of CYH and 4-NQO than are SKY48 and SKY191 on YPD media (FIG. 15). When SKY54 and SKY197 were incubated on Gal/Raff containing media, thereby inducing expression of HXT9 and HXT11 genes, the sensitivity to CYH and 4-NQO increased. The estimated increase of death zone diameters for 4-NQO for SKY54 and SKY 197 on Gal/Raff media in comparison with the parental strains grown on the same media was ~32–40%. After 48 hours of incubation on Gal/Raff media, sensitivity to CYH was estimated to be 0.01 $\mu$g/ml MIC (minimal inhibitory concentration). The MIC is defined as the lowest concentration (micrograms per milliliter of broth) that inhibited visible growth, disregarding a haze of barely visible growth. Sensitivity to CYH of a yeast strain harboring PDR1 and PDR3 deletions, and the HXT11 gene overexpressed from a multicopy plasmid, was previously reported as having an MIC of 0.03 $\mu$g/ml CYH (Nourani et al., 1997, Mol. Cell. Biol. 17:5453–5460). Thus, integrating inducible copies of HXT11 and HXT9 into the chromosome significantly increased the sensitivity of yeast cells to the tested compounds. A comparative analysis of parental strain SKY48 and obtained SKY54 to 73,400 compounds from the SMT chemical library is shown in Table 2. SKY48 is sensitive to 1,959 compounds while SKY54 is sensitive to 3,011 compounds. Thus, SKY54 was sensitive to 154% as many compounds as the parental strain, SKY48.

Thus, the example provided herein this Section, demonstrates the successful construction of a hyperpermeable yeast S. cerevisiae cells, which were engineered by inserting HXT9 and HXT11 into the PDR1 and PDR3 loci, respectively. As shown herein, these cells indeed exhibit increased permeability and sensitivity to a number of exogenously supplied compounds. The yeast strains constructed herein, SKY54 and SKY197, are advantageous for screening for therapeutic compounds in high throughput assays, as described below.

7. EXAMPLE 2

Dual-Bait Yeast Two-Hybrid Screen

The dual-bait two-hybrid system, described in Section 5.2 above, is demonstrated in this Section by the example of a such a screen using the SKY197 strain. Because copies of a lexA operator-controlled LEU2 gene and a cI operator-controlled LYS2 gene are integrated in the yeast chromosome of SKY197, this strain is uniquely suited for such screening assays. Chromosomal integration of these reporter constructs facilitates introduction on extrachromosomal plasmids of target and partner fusion expression vectors required for the dual-bait two-hybrid system.

In particular, the first example provided herein illustrates the use of the yeast two-hybrid system in hyperpermeable SKY197 cells for the identification of compounds that interfere with Ras-Raf interaction, a potentially important drug target for cancer therapy. In the second part of this example, the dual-hybrid two hybrid system is used in the novel hyperpermeable yeast cells of the invention to screen for compounds that interfere with Ras-Raf interactions in a highly specific manner, by utilizing an internal control to select for compounds that disrupt Ras-Raf interactions but do not alter the interaction of the closely related Krit-Krev proteins.

The screening system comprises a SKY197 yeast cell comprising:

(1) integrated chromosomal copies of: a lexA-operator-LEU2 reporter fusion gene; a cI-operator-LYS2 reporter fusion gene; and gal1-inducible copies of HXT9 and HXT11 genes;

(2) a two (2) micron plasmid containing nucleotide sequences of a lexA-operator-LacZ reporter gene;

(3) a two (2) micron plasmid containing nucleotide sequences that encode a LexA-Ras fusion protein, under the control of the ADH promoter region; and (4) a two (2) micron plasmid containing nucleotide sequences that encode an Activation Domain-c-Raf1 fusion protein (AD-cRaf1), under the control of galactose-inducible gal1 promoter.

When SKY-197 yeast cells with the LexA-dfRas fusion gene and the Activation Domain-cRaf1 fusion gene on a two (2) micron plasmid are grown on media with galactose, both fusion proteins are synthesized and form dimers. Such dimer formation results in the activation of transcription of two reporter genes: the lexA-operator-LEU2 gene on the chromosome and the lexA-operator-LacZ reporter gene on the two (2) micron plasmid. As a result, yeast can grow on synthetic dropout medium without leucine and produce a blue color on medium containing XGal.

When cells of this genetic background are contacted with a library of test compounds, those compounds that specifically interfere with the cRaf1:dfRas interaction will disrupt cRaf1:dfRas dimer formation, and transcription from the two reporter genes, LexA-operator-LEU2 and LexA-operator-LacZ will not occur. Under these conditions, the complete loss (or modulation) of activation of the two reporter genes, will result in lac-leu-phenotypes and are, therefore, candidate compounds to be tested in tissue culture models for the reversal of the Ras transforming phenotype.

An internal dual bait hybrid may be included in the system to select against false positive interactions. In this example, the closely related Krev-1 protein is chosen as an alternative target protein, or "bait". Ras-1 and Krev-1 possess 56% amino acid identity and are known to interact with an overlapping set of protein partners (Frech et al., 1990, Science 249: 169–171; Herrmann et al., 1996, J. Biol. Chem. 271: 6794–6800; and Zhang et al., 1993, Nature 364: 308–313.). Raf preferentially interacts with Ras in two hybrid system assay, whereas Kritl preferentially interacts with Krev-1 (Serebriiskii et al., 1997, Oncogene 15: 1043–1049). Neither Ras nor Krev-1 activates transcription when expressed as a DNA binidng domain fusion.

This approach can be comprised of elements (1)-(4), above, and further comprises the following elements:

(5) a two (2) micron plasmid encoding a cI-operator-gusA reporter gene;

(6) a two (2) micron plasmid containing nucleotide sequences that encode a cI-Krev-1 fusion gene, operatively associated with an ADH promoter region; and (7) a two (2) micron plasmid containing nucleotide sequences that encode an Activation Domain-c-Krit fusion protein, (AD-cRaf1) operatively associated with a galactose-inducible gal1 promoter.

When yeast SKY 197 cells containing (1)-(7) are grown on galactose containing media, all four fusion proteins, i.e., cI-dfRas, AD-cRaf1, cI-Krev-1, and AD-c-Krit, are synthesized. Interaction between cI-Ras and AD-cRaf1 causes activation of the lexA-operator-LEU2 gene on the chromosome and the lexA-operator-LacZ reporter gene on the two (2) micron plasmid. In addition, interaction between cI-Krev-1 and AD-c-Krit cause activation of the cI-operator-LYS2 gene on the chromosome and the cI-operator-gusA reporter gene on the two (2) micron plasmid. As in the previous example, such yeast grow on synthetic dropout medium without leucine, and produce a blue color on medium containing Xgal. This strain, in addition, can grow on synthetic dropout medium with lysine, and produce a blue color on media containing X-gluc.

When contacted with a test compound that interferes specifically with Ras/Raf interaction, but not with Krev-1/Krit interaction, the compound would diminish or abolish interaction between cI-dfRas and AD-cRaf1. The loss of this interaction results in loss of transcription activation of the lexA-operator-LEU2 and the lexA-operator-LacZ reporter genes. However, the activity, since the compound does not disrupt the Krev-1/Krit interaction, transcription is still activated from the reporter genes responsive to Krev-1/Krit interaction, i.e., the cI-operator-LYS2 and cI-operator-gusA reporter genes. Thus, such a compound can be detected by selection for LEU–, lacZ– LYS+ gusA+ colonies, i.e., no growth in leucine, white colonies X-gal, growth on lysine, and blue colonies on X-gluc.

Other embodiments of such dual hybrid selection schemes are also possible using various combinations of reporters and expression constructs described herein. Examples and methods for various two-bait dual hybrid selection assays are described in Serebriiskii et al. (1999, J. Biol. Chem. 274:17080–17087), which is incorporated herein by reference in its entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. A yeast cell comprising:
 a) a functional HXT9 hexose transporter gene;
 b) a functional HXT11 hexose transporter gene;
 c) a disrupted PDR1 pleiotropic resistance gene; and
 d) a disrupted PDR3 pleiotropic resistance gene,
wherein the functional HXT9 gene or the functional HXT11 gene is chromosomally integrated into the disrupted PDR1 gene or the disrupted PDR3 gene.

2. The yeast cell of claim 1 wherein the HXT9 gene is chromosomally integrated into the disrupted PDR1 gene.

3. The yeast cell of claim 1 wherein the HXT9 gene is chromosomally integrated into the disrupted PDR3 gene.

4. The yeast cell of claim 1 wherein the HXT11 gene is chromosomally integrated into the disrupted PDR1 gene.

5. The yeast cell of claim 1 wherein the HXT11 gene is chromosomally integrated into the disrupted PDR3 gene.

6. The yeast cell of claim 2 wherein the HXT11 gene is chromosomally integrated into the disrupted PDR3 gene.

7. The yeast cell of claim 3 wherein the HXT11 gene is chromosomally integrated into the disrupted PDR1 gene.

8. The yeast cell of claim 2 wherein the HXT11 gene is chromosomally integrated into the disrupted PDR1 locus.

9. The yeast cell of claim 3 wherein the HXT11 gene is chromosomally integrated into the disrupted PDR3 locus.

10. The yeast cell of claim 1 wherein one or both hexose transporter genes are operatively linked to an inducible promoter.

11. The yeast cell of claim 1 wherein the promoter is selected from a group consisting of a cycI, gal1, gal10, his 3, his4, leu2, and a mat α promoter.

12. The yeast cell of claim 1 further comprising a fusion target protein, a fusion partner protein, and a reporter gene, wherein interaction of the target protein and the partner protein results in the expression of the reporter gene.

13. The yeast cell of claim 12 wherein the reporter gene is LEU2.

14. The yeast cell of claim 12 wherein the reporter gene is lacZ.

15. The yeast cell of claim 12 wherein the reporter gene is LYS2.

16. A method for identifying a test compound that modulates interaction of a target protein and a partner protein comprising the steps of:
 a) contacting the yeast cell of claim 12 with a test compound;
 b) measuring the level of reporter gene expression; and
 c) comparing the level of reporter gene expression in (b) to the level obtained in the absence of said test compound,
such that if the level measured in b) differs from that obtained in the absence of the test compound, a candidate test compound that modulates the interaction of the target protein and the partner protein is identified.

17. The method of claim 16 wherein the reporter gene is LEU2.

18. The method of claim 16 wherein the reporter gene is lacZ.

19. The method of claim 16 wherein the reporter gene is LYS2.

20. The method of claim 16, further comprising:
 d) a second reporter gene, wherein interaction of the target protein and the partner protein results in the expression of the second reporter gene;
 e) measuring the level of second reporter gene expression; and
 f) comparing the level of the second reporter gene expression in e) to the level of the second reporter gene expression obtained in the absence of the test compound,
such that if the level measured in e) differs from the level of expression of the second reporter gene in the absence of the test compound, a candidate test compound that modulates the interaction of the target protein and the partner protein is identified.

21. The method of claim 16 wherein the test compound is a small molecule.

22. The method of claim 16 wherein the target protein is operably attached to a DNA binding domain.

23. The method of claim 22 wherein the DNA binding domain is a cI domain.

24. The method of claim 22 wherein the DNA binding domain is a GAL4 domain.

25. The method of claim 22 wherein the DNA binding domain is an ADH domain.

26. The method of claim 22 wherein the DNA binding domain is a LexA domain.

27. The method of claim 22 wherein the partner protein is operably attached to a transcriptional activation domain.

28. The method of claim 27 wherein the transcriptional activation domain is a Gal4 domain.

* * * * *